(12) United States Patent
Goodman

(10) Patent No.: US 7,544,953 B2
(45) Date of Patent: Jun. 9, 2009

(54) DEVICE FOR PREPARING MICROSCOPY SAMPLES

(75) Inventor: Steven L. Goodman, Madison, WI (US)

(73) Assignee: Microscopy Innovations, LLC, Marshfield, WI (US)

( * ) Notice: Subject to any disclaimer, the term of this patent is extended or adjusted under 35 U.S.C. 154(b) by 198 days.

(21) Appl. No.: 11/752,570

(22) Filed: May 23, 2007

(65) Prior Publication Data

US 2008/0068707 A1 Mar. 20, 2008

Related U.S. Application Data

(63) Continuation of application No. 11/752,239, filed on May 22, 2007, and a continuation of application No. PCT/US2007/069489, filed on May 22, 2007.

(60) Provisional application No. 60/747,928, filed on May 22, 2006.

(51) Int. Cl.
*G01N 1/31* (2006.01)
*G01N 1/36* (2006.01)
*B01L 3/00* (2006.01)

(52) U.S. Cl. .................. 250/440.11; 250/304; 250/307; 356/244; 359/398

(58) Field of Classification Search .......... 250/304, 250/307, 440.11; 356/244; 359/398
See application file for complete search history.

(56) References Cited

U.S. PATENT DOCUMENTS 4,363,783 A * 12/1982 Sitte ........................ 422/63
7,122,155 B2 * 10/2006 Waterbury et al. .......... 422/101

FOREIGN PATENT DOCUMENTS

WO    WO 2006012486 A2 *  2/2006

* cited by examiner

*Primary Examiner*—Jack I Berman
(74) *Attorney, Agent, or Firm*—Alan R. Stewart; Godfrey & Kahn, S.C.

(57) ABSTRACT

A device, method and system for preparing and storing samples for microscopic analysis is disclosed. The device provides a reservoir that can be attached to a displacement pipette thereby filling the reservoir with reagents desired for preparing the samples for microscopic analysis. In some embodiments, the specimen may be contained on a transmission electron microscope (TEM) grid. In other embodiments, the sample may be a light microscope (LM) specimen or a scanning electron microscope (SEM) specimen. In yet another embodiment, the invention provides a method of preparing samples for microscopic examination including a device for preparing TEM grids with, a device for preparing TEM, SEM or LM specimens with and a device for storing both grids and specimens in. In yet another embodiment, the invention provides a system for tracking the preparation, analysis and histological evaluation of multiple samples while also providing for their long term storage.

22 Claims, 20 Drawing Sheets

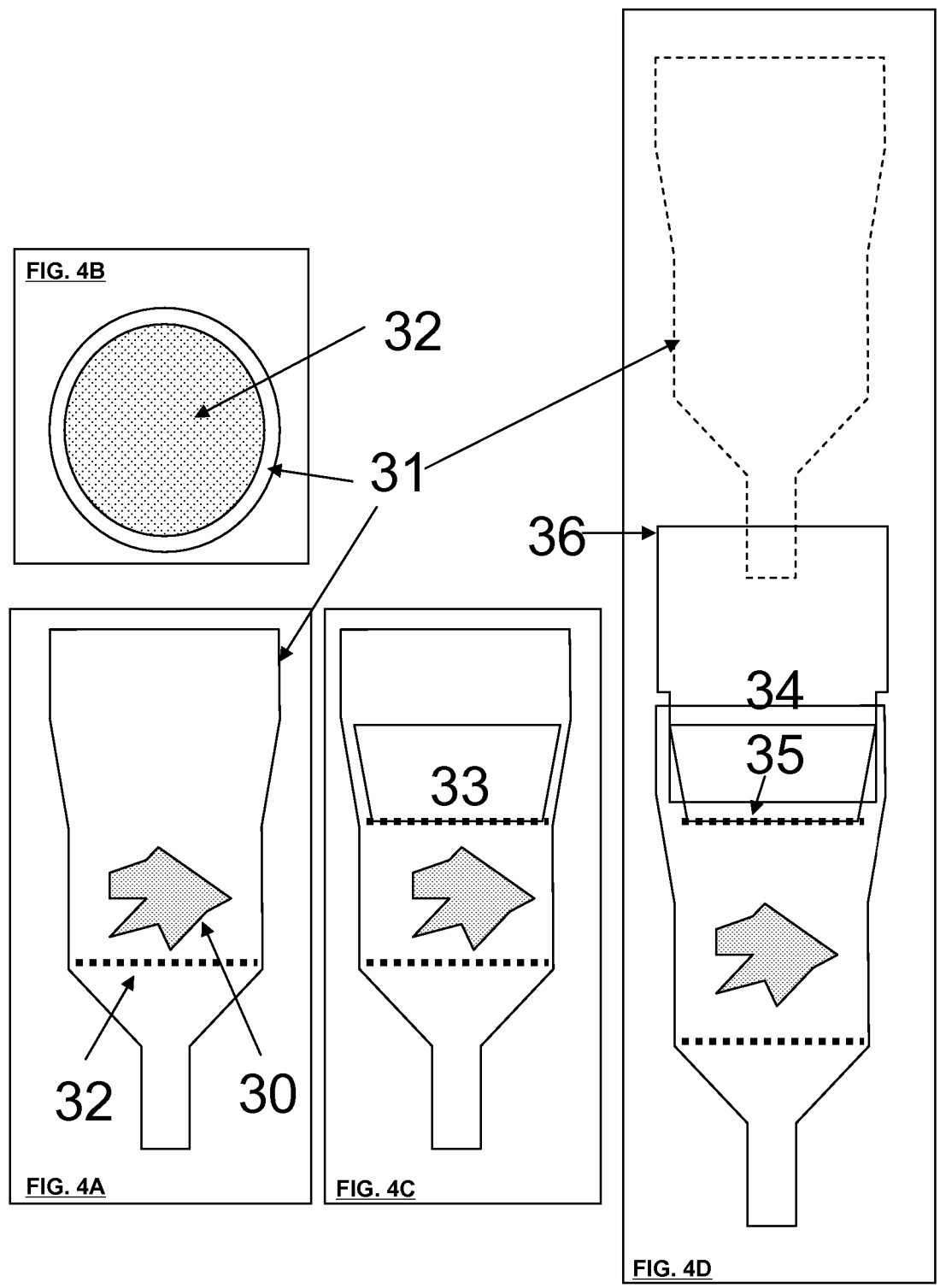

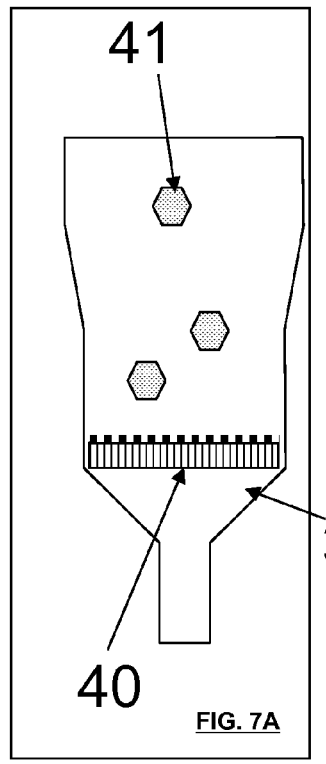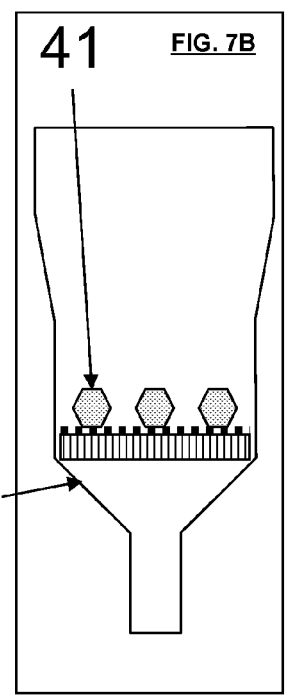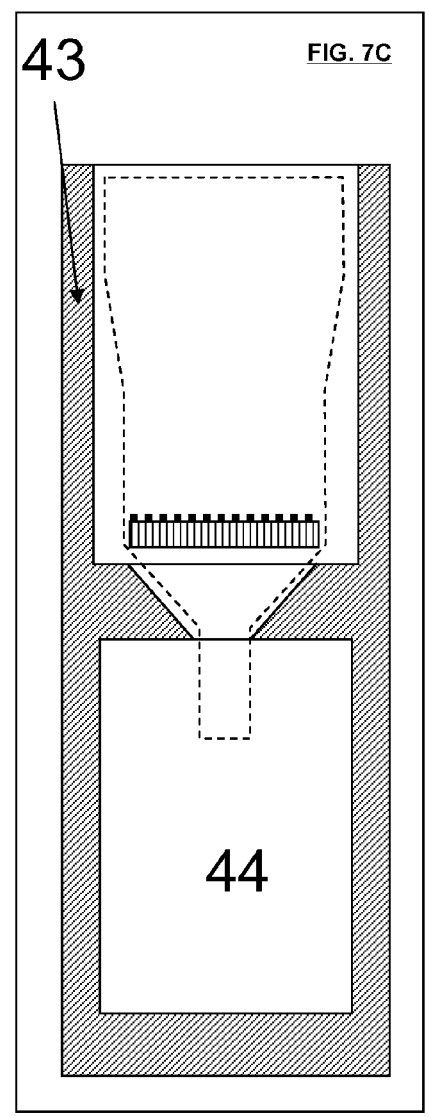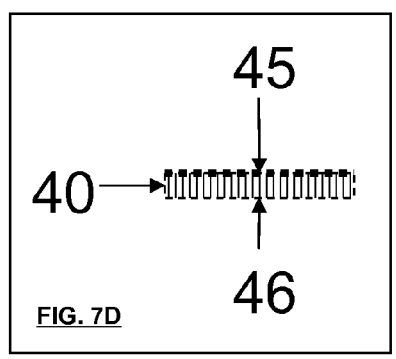

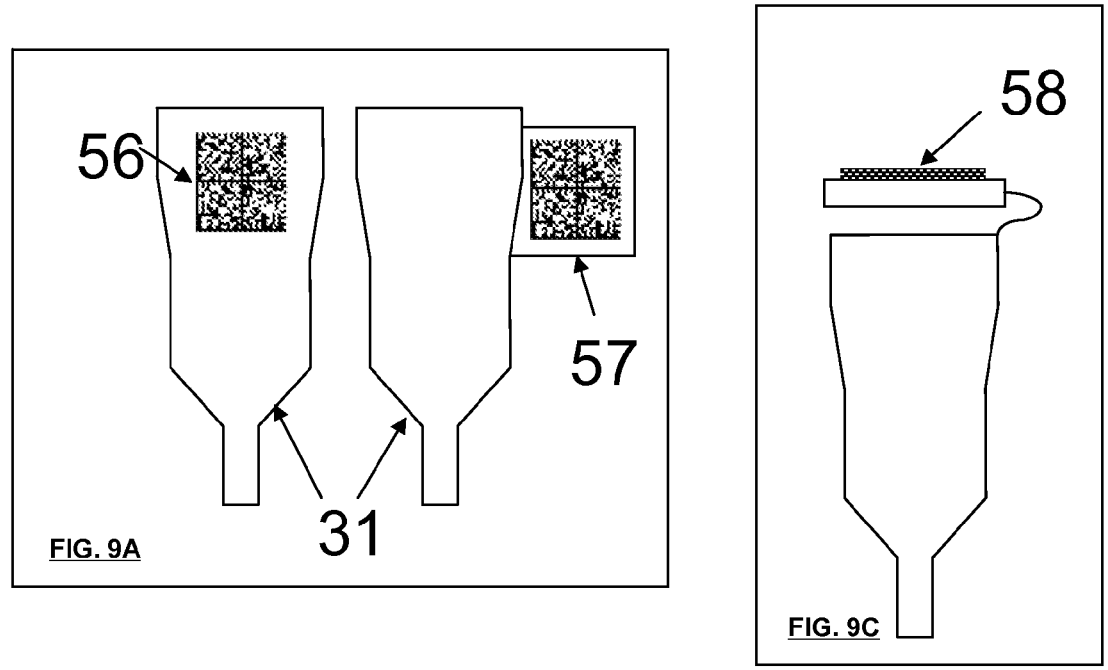
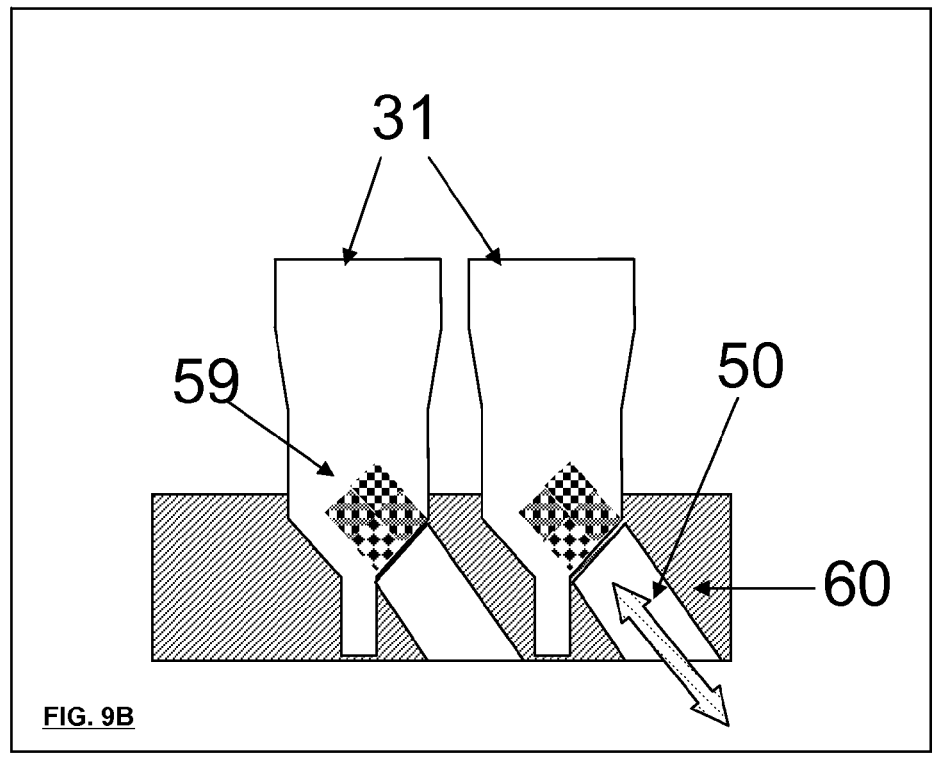

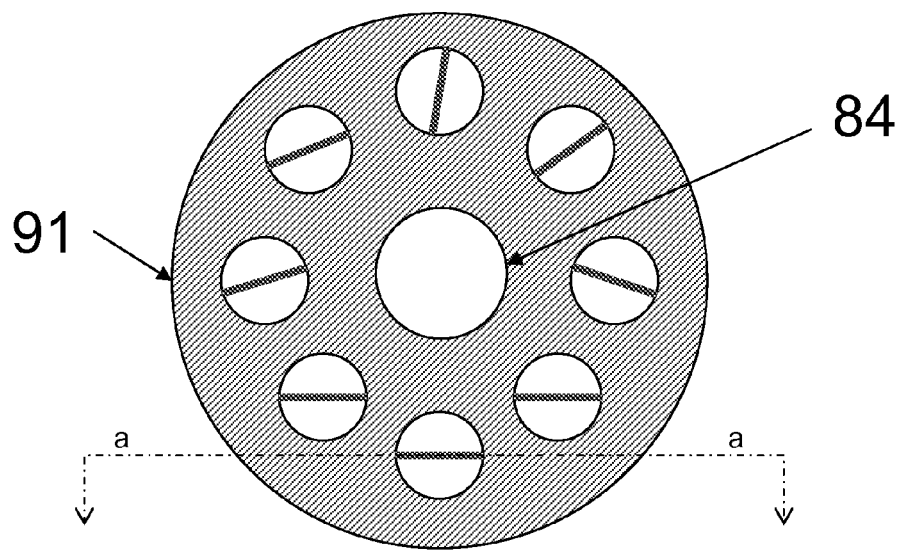
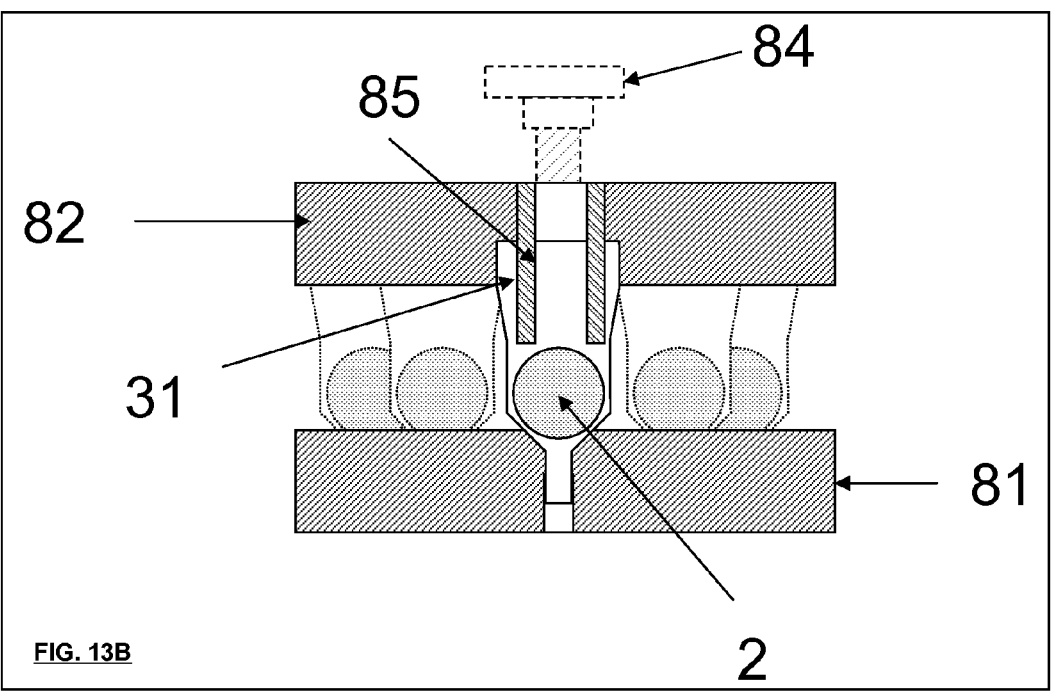

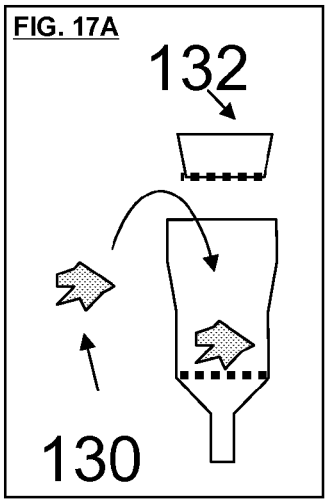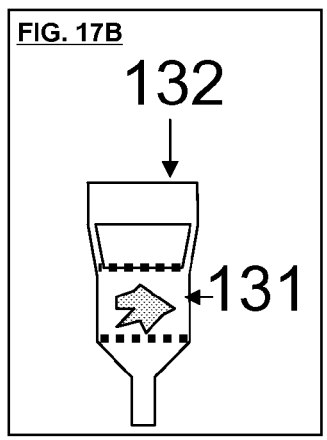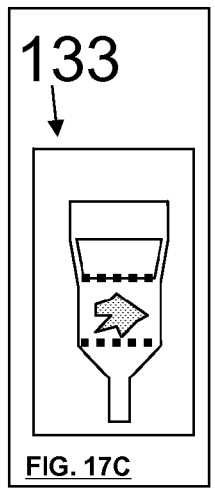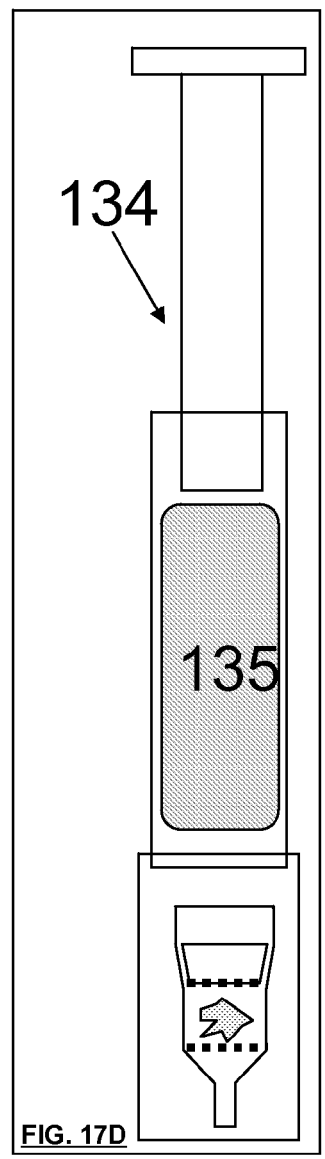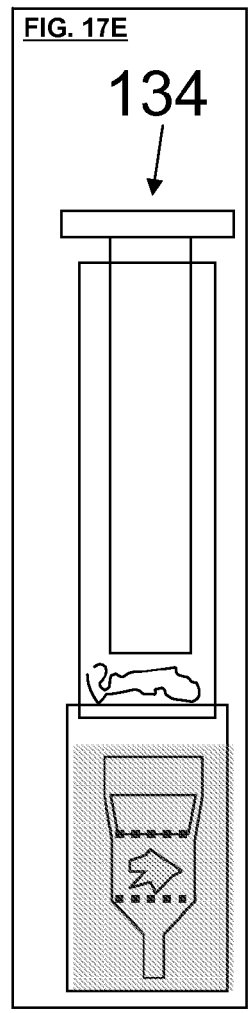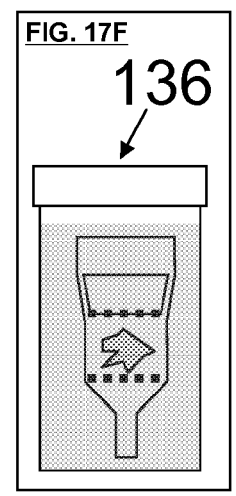

DEVICE FOR PREPARING MICROSCOPY SAMPLES

CROSS-REFERENCE TO RELATED APPLICATION

This application is a continuation of U.S. application Ser. No. 11/752,239 filed May 22, 2007 and international application PCT/US07/69489 also filed May 22, 2007 both claiming priority to U.S. provisional application 60/747,928 filed on May 22, 2006, all of which are incorporated herein by reference in their entirety, for all purposes.

FIELD OF THE INVENTION

This invention is generally directed to a device used to handle and prepare specimens for analysis with light and electron microscopes including especially transmission electron microscopes (TEM), scanning electron microscopes (SEM) and light microscopes (LM).

BACKGROUND OF THE INVENTION

Light microscopes, transmission electron microscopes, scanning electron microscopes and other instruments are extensively used to understand the ultrastructure of a wide variety of synthetic and biological materials in numerous areas of science and technology. For example, light microscopy samples are used for research to identify the development of different organs in animals and plants. In addition, one major use of LM samples is in the histophathologic examination of biopsy samples of tissues suspected of disease. TEM is used to study both biological samples as well as non-biological samples and can even provide atomic scale resolution. TEM is routinely used to investigate metal grain structures, the micro and nano-structures of polymers, semiconductor devices such as computer chips, and to visualize the organelle and molecular organization of cells. Such images are capable of resolution down to approximately 0.1 nm, although this is usually not quite possible with biological materials. TEM and LM specimens are commonly sliced or otherwise prepared into thin cross-sections to enable electrons or photons, respectively, to traverse through the specimen to create an image. SEM is similar to TEMs in that it uses electrons to create an image of the target/sample. However, the resolution of the SEM is typically not as fine as that of the TEM, yet high resolution versions are capable of molecular level resolution of approximately 5 nm. Due to the SEM's ability to image the surface aspect of bulk materials, specimen preparation does not usually entail slicing the specimen into cross-sections.

Study objects for microscopy are prepared in multiple ways depending upon the type of material to be examined, and the type of microscopy to be used. Biological materials require special handling to preserve the structure of the material when it will be examined in the electron microscope, and secondarily to enhance or enable imaging.

Both SEM and TEM instruments perform their imaging in a vacuum (the absence of air or other gases). Since biological materials are generally 50 to 95% water, if these were placed directly within the vacuum the water would evaporate and the specimen would collapse. Consequently both SEM and TEM samples have the water removed after the structure is strengthened with chemicals such as glutaraldehyde, formaldehyde, and osmium tetroxide.

TEM samples must be very thin (typically about 40-100 nm) in order for the electrons used for imaging to be "transmitted" or passed through the sample. To cut specimens into such thin sections the water in the specimen is replaced with plastic that is hardened in place. This plastic supports the sample as it is sliced very thin using a device called an ultra-microtome.

LM specimens, especially those of biological origin, are generally also sectioned in order to provide cross-sections for viewing, and to allow photons (light) to be transmitted through the specimen. As with TEM, LM sections are also embedded to support the specimen during sectioning, however, different generally softer plastics or wax are used as the embedding materials. Water that is frozen with additional materials to enable the ice to be softer, provide better support of the tissue, and reduce ice crystal damage during freezing can also be used.

Because of the delicate nature of microscopy samples and the resolution and power of LM, SEM and TEM analysis, sample preparation requires highly skilled and delicate manipulation. For example, the preparation of LM, SEM and TEM samples may require from between 20 to 40 fluid exchanges. Such samples may be prepared in large quantity and their quality, analysis and identification may have significant downstream impact, such as for biopsy samples, for example. Thus, methods and devices for their preparation have been devised that are either highly cumbersome and/or inadequate for their needs.

For example, U.S. Pat. No. 5,080,869 to McCormick discloses an apparatus and method for preparing samples for histological examination. The device comprises a cassette suitable for holding a sample with perforation in the wall and floor to drain fluid. A stack of such cassettes can be put in a container for the process of fixation. As illustrated by McCormick, inside the container and the cassette are large amounts of dead space resulting in the need for large volumes of fixation media, rinses, and other solutions in order to adequately process the sample. Since many of the chemicals used are noxious and some are expensive to purchase or dispose of, large dead-space volumes are not desirable. In addition, such cassettes are not intended for the preparation and handling of the circa 1 mm specimens typical in biological TEM and many clinical histopathology or biopsy specimens and hence such small specimens can readily become lost or misplaced.

U.S. Pat. No. 5,543,114 to Dudek discloses a unitary biological specimen processing apparatus. The apparatus comprises a container having a lid with apertures in it for straining fluid from the container. As disclosed by Dudek, a sample is placed in the container and fixation fluids entered in one end and emptied out the other end. As can be seen in the Dudek figures, the container has a large volume of dead space in which the sample can be lost or damaged. Further, the sample can not be visually inspected nor can the sample be sectioned or stored in the container.

Similarly, U.S. Pat. No. 7,179,424 to Williamson et al. discloses a cassette for handling and holding tissue samples during processing. As with other, similar devices, the cassette disclosed by Williamson includes a large volume of dead space, and provides little ability to visually inspect the samples within. Further, the cassettes taught by Williamson are not amendable to simultaneous use with other cassettes thus limiting their ability for high-throughput use. In addition, as taught by Williamson et al., the cassettes are complicated devices having relatively high costs and not allowing for sectioning of the sample held within.

Further, most other imaging and analytical methods used to analyze specimens on such small scales could benefit from methods and/or devices that facilitate and standardize the process of preparing such samples. Such applications require the handling, processing, and identification of small specimens for analyses such as, for example, secondary ion mass spectroscopy (SIMS), electron spectroscopy for chemical analysis (ESCA) which is also known as x-ray photoelectron spectroscopy (XPS) and atom probe tomography. Matrix-assisted laser desorption ionization (MALDI), and many other analytical and imaging instrument preparation procedures, are also within the scope of this invention.

Thus, the need exists for a low-cost device and method that allows for the parallel uses of fixation of multiple samples, providing for a high-throughput fixation system that further allows for the tracking and identification of samples held both on a short-term scale and for long-term storage.

Therefore, there is a need for devices and methods to be used in the preparation of TEM grids and specimens for TEM, SEM, LM, SIMS, ESCA, XPS and MALDI that provide for easier preparation of the grids and specimens for analysis and that may allow for more efficient storage and handling.

SUMMARY OF THE INVENTION

A device, method and system for preparing and storing samples for microscopic analysis is disclosed. The device provides a reservoir that can be attached to a displacement pipette thereby filling the reservoir with reagents desired for preparing the samples for microscopic analysis. In some embodiments, the specimen may be contained on a transmission electron microscope (TEM) grid. In other embodiments, the sample may be a light microscope (LM) specimen or a scanning electron microscope (SEM) specimen. In yet another embodiment, the invention provides a method of preparing samples for microscopic examination including a device for preparing TEM grids with, a device for preparing TEM, SEM or LM specimens with and a device for storing both grids and specimens in. In yet another embodiment, the invention provides a system for tracking the preparation, analysis and histological evaluation of multiple samples while also providing for their long term storage.

Therefore, in one embodiment the invention includes a device for preparing microscopy specimens comprising a unitary reservoir; the reservoir having a first end adapted and configured to accept a pipette and a second end having an inlet/outlet therein. In this embodiment, a screen or filter is provided in the second end. In various embodiments, the filter may comprise simply a restricted opening or a plurality of openings. Further, a first reservoir is dimensioned and configured to mate with a second reservoir such that the first end of the first reservoir forms a liquid tight seal with the second end of a second reservoir; and the second end of the reservoir is dimensioned and configured to mate with a pipette tip. Further, in some preferred embodiments the reservoir is adapted to contain a specimen for microscopic evaluation and displacement of the pipette results in filling or emptying of the reservoir with one or more reagents. Thus, filling the reservoir with the one or more reagents prepares the sample for microscopy.

In yet another preferred embodiment, the invention includes a device for preparing specimens for microscopic analysis including a unitary reservoir wherein the reservoir has a first end adapted and configured to accept a pipette and a second end having an inlet/outlet therein. Further included is a screen or filter provided in the second end. In various embodiments the filter may comprise a restricted opening or a plurality of openings. According to this embodiment, a first reservoir is dimensioned and configured to mate with a second reservoir such that the first end of the first reservoir forms a liquid tight seal with the second end of a second reservoir and the second end of the reservoir is dimensioned and configured to mate with a pipette tip. According to this embodiment, the reservoir is configured to contain a specimen for microscopic evaluation and displacement of the pipette results in filling or emptying of the reservoir with one or more reagents. In some preferred embodiments the reservoir includes a protrusion on the inner surface configured to break the surface tension of a liquid held in the reservoir. Thus, filling of the reservoir with the one or more reagents prepares the sample for microscopy.

In yet another embodiment the invention provides a method for preparing specimens for microscopic analysis comprising, placing one or more specimens in a unitary reservoir; the reservoir having a first end adapted and configured to accept a pipette and a second end having an inlet/outlet therein. In this embodiment, a screen or filter is provided in the second end. Further, a first reservoir is dimensioned and configured to mate with a second reservoir such that the first end of the first reservoir forms a liquid tight seal with the second end of a second reservoir; and the second end of the reservoir is dimensioned and configured to mate with a pipette tip. Further included is connecting a displacement device to a first end of the reservoir and passing fixation fluids through the reservoir via displacement of the displacement device such that the specimen has been prepared for microscopic analysis.

In still another preferred embodiment, the invention includes a system for preparing microscopic specimen for analysis comprising, obtaining a specimen, placing the specimen in a unitary reservoir wherein the reservoir has a first end adapted and configured to accept a pipette and a second end having an inlet/outlet therein. Further included is a screen or filter provided in the second end. It should be appreciated that in some embodiments, the filter may comprise a restricted opening while in other embodiments the filter includes a plurality of openings. According to this embodiment, a first reservoir is dimensioned and configured to mate with a second reservoir such that the first end of the first reservoir forms a liquid tight seal with the second end of a second reservoir and the second end of the reservoir is dimensioned and configured to mate with a pipette tip. According to this embodiment, the reservoir is configured to contain a specimen for microscopic evaluation and displacement of the pipette results in filling or emptying of the reservoir with one or more reagents. Further included is identifying the reservoir containing the specimen by the use of a universal product code (UPC), entering information identifying the sample into a laboratory information management system correlated with the UPC; and preparing the sample for microscopic analysis. According to this embodiment, the specimen can be stored in the reservoir for analysis.

These and other features of various exemplary embodiments of the methods according to this invention are described in, or are apparent from, the following detailed description of various exemplary embodiments of the methods according to this invention.

BRIEF DESCRIPTION OF THE DRAWINGS

Various exemplary embodiments of the methods of this invention will be described in detail, with reference to the following figures, wherein:

FIG. 1A is a side-view of one embodiment of a GHMP holding a TEM grid. FIG. 1B is a top-plan view of one embodiment of a GHMP having a wide lumen. FIG. 1C is a top plan view of one embodiment of a GHMP having a narrow lumen. FIG. 1D is a top plan view of a separate embodiment of a GHMP having a narrow lumen. FIG. 1E is a one embodiment of the invention being adapted to hold multiple grids.

FIG. 2A is a side plan view of a GHMP holding a grid and being capped by a plug. FIG. 2B IS a side plan view illustrating the orientation the presence of an inspection window while line "a" illustrates the coupling section of the GHMP, line "b" illustrates the grid holding section and line "c" illustrates the inlet/outlet (i/o) section. FIG. 2C is a side-plan view of the embodiment shown in FIG. 2B turned 90 degrees. FIG. 2D is a top-plan view of FIG. 2B. FIG. 2E is a top-plan view of FIG. 2C showing a low volume GHMP holding a transmission electron microscope grid that can be viewed with visual clarity.

FIG. 4 is a schematic representation of another embodiment of the invention optimized for holding specimens in preparation for study, a specimen holder micropipette device (SHMP). FIG. 4A is a side-plan view of the SHMP holding a specimen. FIG. 4b is a top plan view of the embodiment shown in FIG. 4A. FIG. 4C is a side plan view of one embodiment of the invention showing a retaining plug inserted in the SHMP. FIG. 4D shows yet another embodiment of the invention wherein the specimen is held in the SHMP via the unitary screen or filter at the i/o end and via a retaining screen at the coupling section and further with a long plug coupled to the SHMP. Also shown is the modular feature by which a second SHMP (or GHMP) can fit into the long plug.

FIG. 5A shows a flat bottomed SHMP having an in-molded screen or filter. FIG. 5B is a top-plan view of the SHMP shown in FIG. 5A. FIG. 5C shows the coupling of various SHMPs (or GHMPs) coupled together with a conventional pipette tip. As illustrated, SHMPs can have any desirable shape, e.g., flat, wedged, chisel, etc.

FIG. 6A shows the SHMP resembling a box or cassette. FIG. 6B shows the SHMP inserted in a conventional or specially designed pipette tip (referred to herein as a specimen holder pipette insert (SHPI)). FIG. 6C illustrated multiple SHPIs inserted in a pipette tip. FIG. 6D illustrates one method of loading an SHPI.

FIGS. 7A-7D illustrate one embodiment of the invention optimized to hold multiple specimens. FIG. 7A is a side plan view showing an SHMP with multiple specimens placed inside for fixation. FIG. 7B illustrates the attachment of the specimens shown in FIG. 7A. FIG. 7C illustrates one embodiment of the invention having an adapter designed to allow filtration via centrifugation. FIG. 7D illustrates the removable screen of FIG. 7A designed to be used as a microscopic grid.

FIGS. 9A-9C are schematic diagrams showing various embodiments of the invention illustrating the use and position of machine readable codes, such as bar codes in conjunction with the GHMPs and SHMPs.

FIG. 12A is a side-plan view while FIG. 12B is a top-plan view of the same embodiment.

FIGS. 13A and 13B are schematics showing a separate embodiment of the invention including a multiple micropipette processing device according to the invention. FIG. 13A is a top-plan view while FIG. 13B is a side plan view cut-away through lines a-a.

FIG. 15A shows an SHMP held in a microtome chuck. FIG. 15B shows the SHMP, including the fixed specimen begin cut in the microtome. FIG. 15C shows the microtome making serial slices through the SHMP/specimen.

FIG. 16A is a side-plan view showing multiple SHMPs arranged in a base suitable for processing by automatic processor or robotic pipetters. FIG. 16B is a top-plan view of the embodiment shown in FIG. 16A. FIG. 16C is a side plan view illustrating that different embodiments of the reservoir, both SHMP and GHMP can be used in the base.

FIG. 17A-17F are schematic diagrams showing the utility of SHMPs in remote or field locations, including use of appropriate fixative ampoule and storage vials. FIG. 17A shows the use of an SHMP to collect samples in the field the SHMP compatible with a plug or cap to retain the sample. FIG. 17B shows the specimen safely retained in the SHMP. FIG. 17C illustrates a container suitable to hold the SHMP. FIG. 17D shows the use of an apparatus useful for injecting the contents of an ampoule holding a fixation reagent into the container holding the SHMP. FIG. 17D, shows the rupture of the ampoule with the, possibly noxious, contents injected into the container. FIG. 17E shows the container safely capped with the sample contained in the fixation reagent.

DETAILED DESCRIPTION OF THE EXEMPLARY EMBODIMENTS

Figure 1:
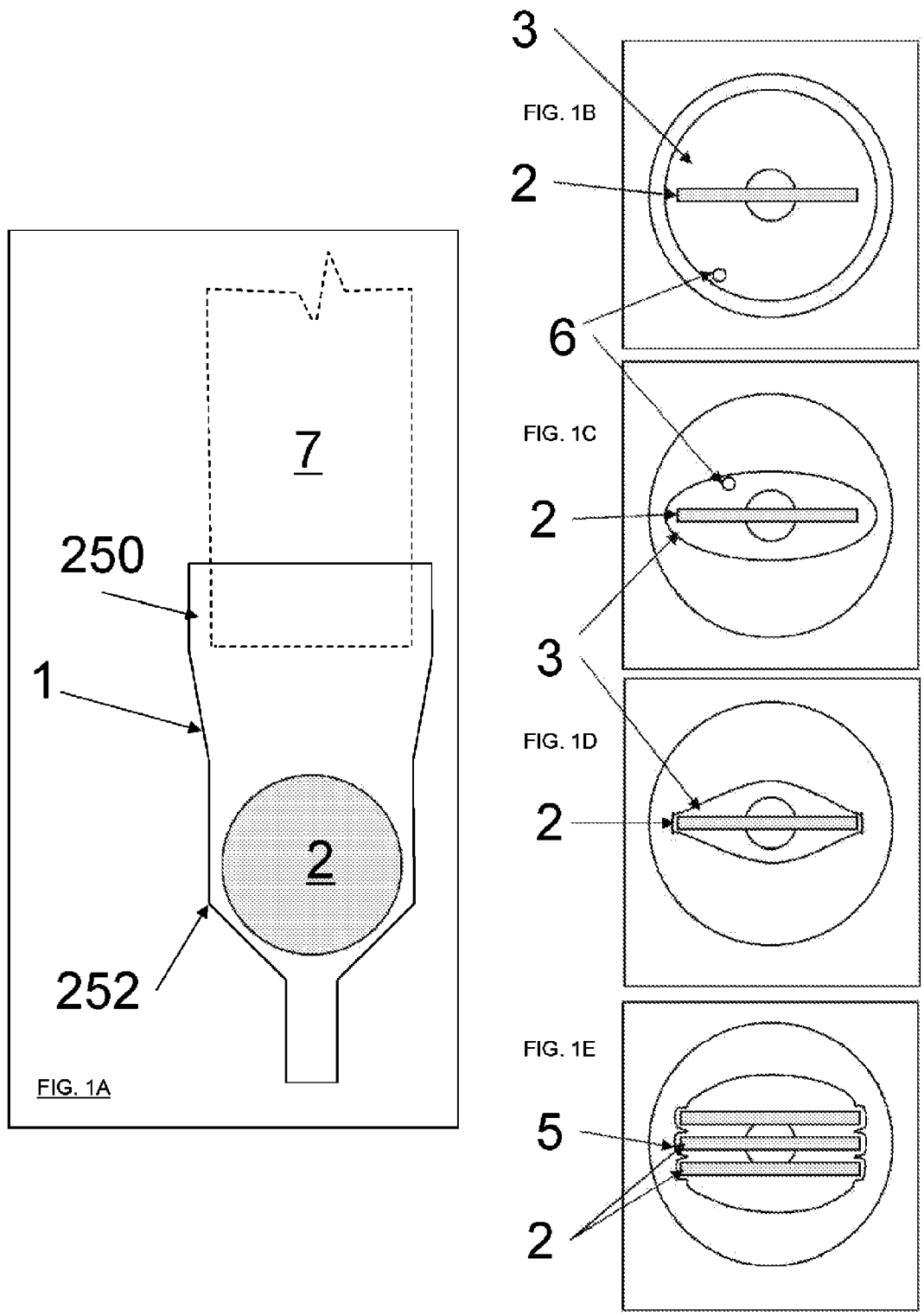
FIGS. 1A-1E are schematic diagrams of various exemplary embodiment of the invention showing various reservoirs or grid holding micropipette device (GHMP) holding a transmission electron microscope grid.

A device, method and system for preparing and storing samples for microscopic analysis is disclosed. The device provides a reservoir that can be attached to a displacement pipette thereby filling the reservoir with reagents desired for preparing the samples for microscopic analysis. In some embodiments, the specimen may be contained on a transmission electron microscope (TEM) grid. In other embodiments, the sample may be a light microscope (LM) specimen or a scanning electron microscope (SEM) specimen. In yet another embodiment, the invention provides a method of preparing samples for microscopic examination including a device for preparing TEM grids with, a device for preparing TEM, SEM or LM specimens with and a device for storing both grids and specimens in. In yet another embodiment, the invention provides a system for tracking the preparation, analysis and histological evaluation of multiple samples while also providing for their long term storage.

Before the present invention is described, it is understood that this invention is not limited to the particular embodiments described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing sample preparation methods, instruments and methodologies which are reported in the publications which might be used in connection with the invention. Nothing herein is to be construed as an admission that the invention is not entitled to antedate such disclosure by virtue of prior invention. Further, it should be appreciated that as used herein, screen and filter are used interchangeable such that, in some instance screen or filter refers to a restricted opening in the second end of the reservoir while in other embodiments the screen or filter comprises a plurality of opening in the second end of the reservoir. Further, as described herein the GHMP and SHMP devices comprise reservoirs adapted to contain analytical specimens thus, the terms "GHMP", "SHMP" and "reservoir are used interchangeably.

The invention provides devices, methods and systems for preparing and storing samples for microscopic analysis. The device provides a reservoir that can be attached to a displacement pipette thereby filling the reservoir with reagents desired for preparing the samples for microscopic analysis. In some embodiments, the specimen may be contained on a TEM grid. In other embodiments, the sample may be a light microscope specimen or an SEM specimen. In still other embodiments, the sample may be SIMS, ESCA, XPS or MALDI specimens. In yet another embodiment, the invention provides a method of preparing samples for microscopic examination including a device for preparing TEM grids with, a device for preparing TEM specimens with and a device for storing both grids and specimens in. In yet another embodiment, the invention provides a system for tracking the preparation, analysis and histological evaluation of multiple samples while also providing for their long term storage. In these embodiments the samples may be used as specimens for TEM, SEM, LM, SIMS, ESCA, XPS and MALDI analysis.

Therefore, in one embodiment the invention includes a device for preparing microscopy specimens comprising a unitary reservoir; the reservoir having a first end adapted and configured to accept a pipette and a second end having an inlet/outlet therein. In this embodiment, a screen provided in the second end. Further, a first reservoir is dimensioned and configured to mate with a second reservoir such that the first end of the first reservoir forms a liquid tight seal with the second end of a second reservoir; and the second end of the reservoir is dimensioned and configured to mate with a pipette tip. Further, in some preferred embodiments the reservoir is adapted to contain a specimen for microscopic evaluation and displacement of the pipette results in filling or emptying of the reservoir with one or more reagents. Thus, filling the reservoir with the one or more reagents prepares the sample for microscopy.

In yet another preferred embodiment, the invention includes a device for preparing specimens for microscopic analysis including a unitary reservoir wherein the reservoir has a first end adapted and configured to accept a pipette and a second end having an inlet/outlet therein. Further included is a screen provided in the second end. According to this embodiment, a first reservoir is dimensioned and configured to mate with a second reservoir such that the first end of the first reservoir forms a liquid tight seal with the second end of a second reservoir and the second end of the reservoir is dimensioned and configured to mate with a pipette tip. According to this embodiment, the reservoir is configured to contain a specimen for microscopic evaluation and displacement of the pipette results in filling or emptying of the reservoir with one or more reagents. In some preferred embodiments the reservoir includes a protrusion on the inner surface configured to break the surface tension of a liquid held in the reservoir. Thus, filling of the reservoir with the one or more reagents prepares the sample for microscopy.

In yet another embodiment the invention provides a method for preparing specimens for microscopic analysis comprising, placing one or more specimens in a unitary reservoir; the reservoir having a first end adapted and configured to accept a pipette and a second end having an inlet/outlet therein. In this embodiment, a screen provided in the second end. Further, a first reservoir is dimensioned and configured to mate with a second reservoir such that the first end of the first reservoir forms a liquid tight seal with the second end of a second reservoir; and the second end of the reservoir is dimensioned and configured to mate with a pipette tip. Further included is connecting a displacement device to a first end of the reservoir and passing fixation fluids through the reservoir via displacement of the displacement device such that the specimen has been prepared for microscopic analysis.

In still another preferred embodiment, the invention includes a system for preparing microscopic specimen for analysis comprising, obtaining a specimen, placing the specimen in a unitary reservoir wherein the reservoir has a first end adapted and configured to accept a pipette and a second end having an inlet/outlet therein. Further included is a screen provided in the second end. According to this embodiment, a first reservoir is dimensioned and configured to mate with a second reservoir such that the first end of the first reservoir forms a liquid tight seal with the second end of a second reservoir and the second end of the reservoir is dimensioned and configured to mate with a pipette tip. According to this embodiment, the reservoir is configured to contain a specimen for microscopic evaluation and displacement of the pipette results in filling or emptying of the reservoir with one or more reagents. Further included is identifying the reservoir containing the specimen by the use of a universal product code (UPC), entering information identifying the sample into a laboratory information management system correlated with the UPC; and preparing the sample for microscopic analysis. According to this embodiment, the specimen can be stored in the reservoir for analysis.

TEM imaging is sensitive to the atomic number of the elements in the specimen. This requires that many samples be stained or labeled with atoms that have higher atomic numbers than those found in biological materials (mostly carbon, oxygen, nitrogen, phosphorus and hydrogen). The staining and labeling elements usually used include osmium (which also provides strength to the sample), uranium, lead, and iron.

LM samples also require staining to improve contrast. These stains are often organic and inorganic dyes, fluorescent dyes, and other specialty labels.

SEM samples have their water removed after strengthening with glutaraldehyde, formaldehyde, and/or osmium tetroxide using procedures and chemicals that allow dehydration to occur without the surface tension forces that would otherwise cause the specimen to collapse from a "grape to a raisin." The most common method is drying with the critical point method using a device called a critical point dryer. Other procedures can also be used including specialized freeze drying procedures and drying from special chemicals which minimize these surface tension forces.

TEM specimens are prepared by slicing, cutting, grinding, sputtering, and/or other means to prepare very thin specimens of the material of interest. Typically, such specimens prepared for examination (study objects) are about 20-100 nanometers thin or perhaps up to about 1-10 micrometers thick. These study objects are placed on very thin specially made screen-like supports called TEM grids. These grids are analogous to the glass slides used to support study objects in light microscopy. TEM grids are generally a standard diameter of 3 mm (or sometimes 3.05 mm and rarely about 2 mm) and are made of very thin films of Ni, Cu, Au, Mo, metal alloys, or some other materials such as polymers (e.g. nylon), carbon, or Be for some specialized applications. The grid is used to support the study object during processing and subsequently during TEM imaging. The grid helps hold the specimen (relatively) flat during TEM examination or other analyses including light microscopy, SEM, other microscopies, and for additional imaging and analytical instruments. In transmission microscopies (e.g. TEM and light microscopy), those portions of the study object that overlie holes or openings in the grid are viewable.

Due to the thinness of the TEM grid, typically 20-50 µm thick, they are very fragile, difficult to handle, and readily bent. Bending of the grid can damage the study object or cause it to fall off, and makes imaging more difficult due to the resulting variations in the study object focal plane in the TEM. In addition, due to their small size, grids are easily dropped and often lost during handling. This is particularly problematic with rare or valuable study objects as well as with many other specimens since it may take hours or even days to perform the multiple processing steps to prepare a study object for examination. Processing protocols vary extensively, but may typically include chemical fixation, applications of multiple chemical stains, intermediate rinses, exposure to biological reagents such as antibody labels, chemical or solvent etchants, dehydration processing with alcohols or other solvents, rapid freezing and other cryogenic treatments, embedding in a resin sectioning with a microtome and elevated pressure treatments including a common protocol known as the critical point method that is used as part of dehydration protocols. This is only a partial list since there are many additional protocols and procedures known to those skilled in the art, and since new protocols and modification of existing protocols are developed for new studies. Typically, in current practice, the grid is manually transferred from one solution or treatment to the next using fine forceps (tweezers). Since with each transfer there is a finite risk of loss or damage, several different apparati have been described to minimize the potential loss or damage, and to reduce the time and effort required for simultaneous processing of several grids at once.

The entire process of fixing, rinsing, embedding, staining and other treatments used in preparing biological (and some non-biological) specimens for TEM and LM often requires that the specimen is treated with over 40 fluid exchanges. SEM specimen preparation, especially biological materials, typically requires over 20 fluid exchanges. Since specimens are very small, generally about one cubic millimeter in size and often not visible to the naked eye, it is extremely easy to lose, misplace, damage and misidentify specimens during this multi-step processing.

Apparatus for processing grids are found in a large variety of designs and utilities. The most common type is a flat polymeric, glass, or ceramic substrate or dish a few centimeters in size that has small depressions or wells in its surface (typically 0.5-1 cm) to hold droplets of fluid (stains, rinses, etc), into which the grids are immersed. A variant of these plate-type wells are those that are fabricated from a strongly hydrophobic material so that the fluid, which is usually aqueous or sometimes a solvent such as ethanol, rounds up into droplets that engulf the grid. Many TEM users simply perform staining by placing a droplet of an aqueous stain on a small sheet of polyethylene film (e.g. Parafilm) to provide a hydrophobic surface. Commercial versions of these simple devices include the Electron Microscopy Sciences (EMS) staining plate, the PELCO (Ted Pella Inc.) immunostaining pad, the PELCO (Ted Pella Inc.) Mesa staining pad, and the Quad 9 square Grid Gripper (Structure Probe Inc.). The grid is processed from one solution to the next by manually picking it up with forceps and placing it in a droplet of the next solution. Alternatively, pipettes can be used to siphon off (remove) the first solution and replace it with a second. A variation of these pads or plates are elastomeric polymeric substrates in which a slit is cut into the polymer surface so that the edge of a grid can be inserted into the slit to hold it perpendicular to the support. An example of this type of device is the Chien Staining Pad (Ted Pella Inc.). The grid is held in place by compression from the elastomer, much as if the grid is being held by forceps. The grid is processed from one solution to the next by changing the reagents within the bathing chamber of the device. All these aforementioned devices are typically a several square centimeters in size and generally do not provide an integral cover. Consequently, evaporation and atmospheric interaction with the reagents can be problematic. Many offer numbering or other indexing schemes to enable the identification of individual grids. However, it is easy to misplace and/or lose grids during the required handling. Elastomer-based clamping is variable in holding strength depending upon the depth of insertion into the slot. Moreover, the holding strength can weaken over time due to chemical interactions with staining or processing reagents. Thus, grids are not always securely held and may fall out of their designated ordered location leading to misidentification, or may become lost.

The above devices are generally adaptable to specimen preparation protocols that require simple fluid exchanges such as most routine chemical and biological staining. However, these devices are problematic for other protocols such as certain common liquid and vapor staining procedures that use aggressive reagents (e.g. $OsO_4$ or $RuO_4$) that will permanently stain and possibly damage these devices. These devices are also not convenient nor suitable for dehydration protocols (e.g. graded ethanol treatments) since specimens will tend to air-dry during fluid exchanges during the time after one fluid is expelled and before the second fluid is introduced since the open nature of some of these devices permits rapid evaporation of solvents such as ethanol that tend to evaporate very quickly. These devices are similarly not suitable for critical point drying procedures such as with supercritical $CO_2$ due to their large size and slow fluid exchange, nor for cryogenic procedures since their large size (relative to a grid) and consequently high (thermal) mass impede rapid cooling. Moreover, such devices also do not provide adequate flow rates of cryogenic fluids to the study object to enable a sufficiently high rate of cooling. Devices that utilize elastomeric compression to hold grids are also not suitable for these procedures since the elastomeric materials will lose their elastomeric or compression property at low temperatures, and/or during exposure to many aggressive reagents (e.g. $OsO_4$, $RuO_4$, high pressure $CO_2$, some solvents) thus causing the study objects to be detached from their indexed location or perhaps even entirely lost.

Apparatus for preparing specimens for LM, TEM, SEM SIMS, ESCA, XPS and MALDI come in a variety of forms. Mostly commonly, specimens are held in vials, dishes, or small bottles as they are treated sequentially with various reagents. The use of open bottles and vials enables careful control of procedures, however such processing is usually wasteful and specimens are prone to loss or damage. An alternative to simple vials or dishes to hold specimens for LM and histopathology processing is to use cassettes to hold tissue specimens as this reduces the risk of loss or damage. The cassettes, such as those described above and disclosed by McCormick and Williamson are then transferred from reagent to reagent either manually or automatically with dedicated instruments.

Some devices are available for automatic processing. For example, instruments such as the Tissue-Tek® TEC™ 5 (Sakura Finetek USA, Inc) and the Leica ASP300 S (Leica Microsystems, Inc.) are available. For electron microscopy, there are similar automated tissue processors such as the RMC Baltec EMP 5160 (BAL-TEC AG), the EMS LYNX (Electron Microscopy Sciences, Inc.) or the SPI FastCat™ (Structure Probe, Inc.). These can process approximately 50 specimens at a time with each held in individual porous cassettes that are significantly smaller than the histopathology cassettes, for the majority of fixation and embedding steps. The automatic devices provide convenience but are prohibitively expensive for all but the largest uses. Further, such automatic devices require relatively more liquid volume than manual processing, and require reservoirs of reagent, hence such devices are wasteful especially if they are not utilized on a daily basis. In addition such waste may be compounded especially if very expensive reagents, such as antibody labels, or extremely toxic or noxious reagents such as $RuO_4$, are used since these may damage these expensive instruments. Additionally, automatic processors do not enable many important processing methods including microwave fixation and cryogenic protocols. Automated processors and vial processing also do not enable integral embedding of specimens, so specimens must be removed from the vial or cassette and then placed in an embedding capsule or flat embedding tray for final embedding. While cassettes may be labeled to positively identify and track a specimen processed with vial and automatic processing, such instruments and methods do not provide a label through all specimen preparation steps since specimens must be removed from cassettes for several steps, such as final embedding.

A device and method and system for preparing and storing samples for microscopic analysis is disclosed. The device provides a reservoir that can be attached to a displacement pipette thereby filling the reservoir with reagents desired for preparing the samples for microscopic observation. In some embodiments the sample may be a transmission electron microscope grid. In other embodiments, the sample may be a microscope specimen. In yet another embodiment, the invention provides a method of preparing samples for microscopic examination including a device for preparing TEM grids, a device for preparing TEM, SEM, LM, SIMS, ESCA, XPS and MALDI specimens with and a device for storing both grids and specimens in.

EXAMPLE 1

Grid Holding Micropipette Device and Sample Holding Micropipette Device

One embodiment of the invention is shown in FIGS. 1A-1E. As shown in FIG. 1A a reservoir such as a tapered tube-shaped holder 1 accepts an individual TEM grid 2 (or similar study object) within its lumen. Each grid 2 is held at its periphery by the taper or size of the tube, and/or by small protrusions within the tube so that the grid 2 is held by its edges such that the study objects on the grid face are protected from damaging contact with the tube wall. A number of profiles can be used to hold the grid 2 and prevent contact of the grid faces (flat aspects) with the sides of the tube. Lumens 3 that are broad or open as shown in FIG. 1B, provide for improved flow as may be desired with higher viscosity reagents or where rapid fluid exchange is desired, while lumens 3 having a more narrow shape reduce the volume required for staining or other treatments and/or more securely prevent grid motion as shown in FIGS. 1C and 1D. Multiple protrusions 5 can enable the holding of more that one grid within the tube, FIG. 1E. In various embodiments, small protrusions 6 in the inner face of the GHMP reservoir can also be placed within the lumen to facilitate capillary filling by "breaking" surface tension. The top or first end 250 and second end 252 of the tapered GHMP reservoir 1 is designed for fitting with a pipette device 7, such as a commercial automatic device commonly referred to as a Pipetteman® (Gilson, Inc.) or a similar pipette device, or a syringe, or an automated liquid handling device or system. Intermediate couplers (not shown) can also be used to join with other devices. In the simplest use, the pipette device is used to introduce and expel fluids from the grid holding tube or micropipette GHMP 1, to enable staining or other processing (e.g. micropipette processing device). The GHMP 1 enables substantially all grid specimen preparation procedures and grid storage to be accomplished within the GHMP 1. This greatly reduces the manual handling of individual grids, thus greatly reducing damage, loss, misplacement and misidentification.

It can be seen that the basic design of the GHMP 1 provides excellent protection from damage. Using a slot to hold grids provides higher security over holders that depend on adhesive or clamps since slots are more secure. Grids can work loose from clamps, and clamps are more prone to operator errors such as clamping over the study object or insufficient placement of the grid in the clamp so that it is not held properly. Clamps, such as polymer slits have variable strength, and certain chemical treatments such as oxidants and cross-linkers and others used to stain or fix specimens will damage the polymer rendering it less elastic. Similarly, using an adhesive coating to hold grids in place is problematic since if a grid is placed on the adhesive substrates it is all too easy for there to be improper placement of the specimen so that it may stick to the adhesive. It is also possible for specimen support polymers that are routinely applied to grids (e.g. Formvar®) or carbon films, to stick to the adhesive thus leading to specimen loss or damage. Those familiar with the art will recognize that it is often not easy to tell which side of the grid contains the study object hence this is a very common problem. Devices where grids are held within slots do not have these problems. However, achieving good fluid flow within such slots can be difficult. However, the GHMP design places the grid in the center of a flow field thereby providing excellent fluid contact between the grid (with the attached study object) and the treatment fluid.

FIGS. 2A-2E show a grid held in a tapered low volume GHMP 4 from different viewpoints. FIG. 2A, shows a retainer or plug 20 that can be used to hold the grid in place, such as for storage or during certain processing steps. In the embodiment of the invention illustrated in FIG. 2A the retainer or plug 20 is solid, it should be appreciated that the plug 20 can be produced to enable fluid or vapor exchange, such as with a thru bore. Such plugs 20 thus retain the grid 2 or other specimen. Thus, it should be appreciated that the plug or retainer 20 can also be integral, or one piece, with the GHMP. Since it may be desirable to view processes occurring inside the GHMP, in some preferred embodiments, the sides 21 of the GHMP 4 are flat, as shown in FIGS. 2D and 2E and transparent, as shown in FIGS. 2B and 2C, for optical microscopy, or transparent to the appropriate radiation for spectroscopy. For example, this would enable dynamic light microscopy to monitor biologic or non-biologic events occurring on the grid which can then be processed for electron microscopy and then subsequently examined at high resolution with an electron microscope. Another example would be to monitor processing treatments or to measure the effects of such treatments during processing, for example, monitoring the uptake of stains or the removal of water or other materials from the study object. In a further embodiment, shown in FIG. 3, the GHMPs 22 are designed and configured to be stackable with each other. As shown in this embodiment, multiple GHMPs 22 can be fitted together, having a micropipette 7 fitted as the last stage for preparation of multiple GHMP samples at time. Also shown, the bottom GHMP 22 is fitted to a special or standard tapered pipette tip 23 for greater ease of pipetting fixation fluids into the GHMP 22.

Whilst grids should generally be held on edge, other types of specimens or study objects need not be so held, such as small bulk specimens 30 which are shown in FIGS. 4A, 4C and 4D. This embodiment may be referred to as a Specimen Holder Micro-Pipette or SHMP 31. A screen or filter or similar structure 32 that enables fluid transmission yet retains the specimen 30 is incorporated in the bottom of the SHMP 31 to retain the specimen 30 within the SHMP 31. This is illustrated in FIG. 4B, which shows a top plan view of the SHMP 31 shown in FIG. 4A. A screen or filter or similar structure is then incorporated into a retaining plug or cap 33 that is fully inserted into the SHMP 31. In some embodiments, shown in FIG. 4D, a longer plug or cap 34 with a retaining screen or filter 35 extends from the SHMP so that plug/screen 34/35 is readily removed from the SHMP to insert/remove the specimen. In some embodiments, the top the plug 34 is shaped to join with pipettes or other devices (not shown), or to enable stacking of multiple SHMPs and/or GHMPS 31.

Alternatively, those of skill in the art will appreciate that the plug 35 and a coupling adaptor 36 can be shaped and used as separate units to be used in any combination. It should be noted that SHMPs 3 and GHMPs 1 may be generally interchanged in the subsequent discussion since the principle distinction is the type or shape of specimen that is contained. Certain embodiments of SHMPs can be larger or smaller than GHMPs since grids are produced in fixed sizes while other types of specimens may be larger or smaller. These SHMPs may be used as the mold for embedding study objects within resins to enable sectioning for TEM (and other microscopies and analyses). The size and shape of the SHMP is comparable to molds currently used for this purpose. Resins can be cured directly within the SHMP and then the SHMP is cut away or the cured resin is removed from the top to reveal the embedded specimen ready for sectioning.

FIG. 5 illustrates the compatibility of GHMPs or SHMPs for use with each other. SHMPs can be stacked with one SHMP 37 providing the screen or filter element 32 to entrap the specimen held within a second SHMP 38. Separate screens and plugs may also be used such as screens and plugs 33, 34/35 shown in FIGS. 4C and 4D. Stacking of SHMPs enables simultaneous processing of multiple specimens.

Figure 2:
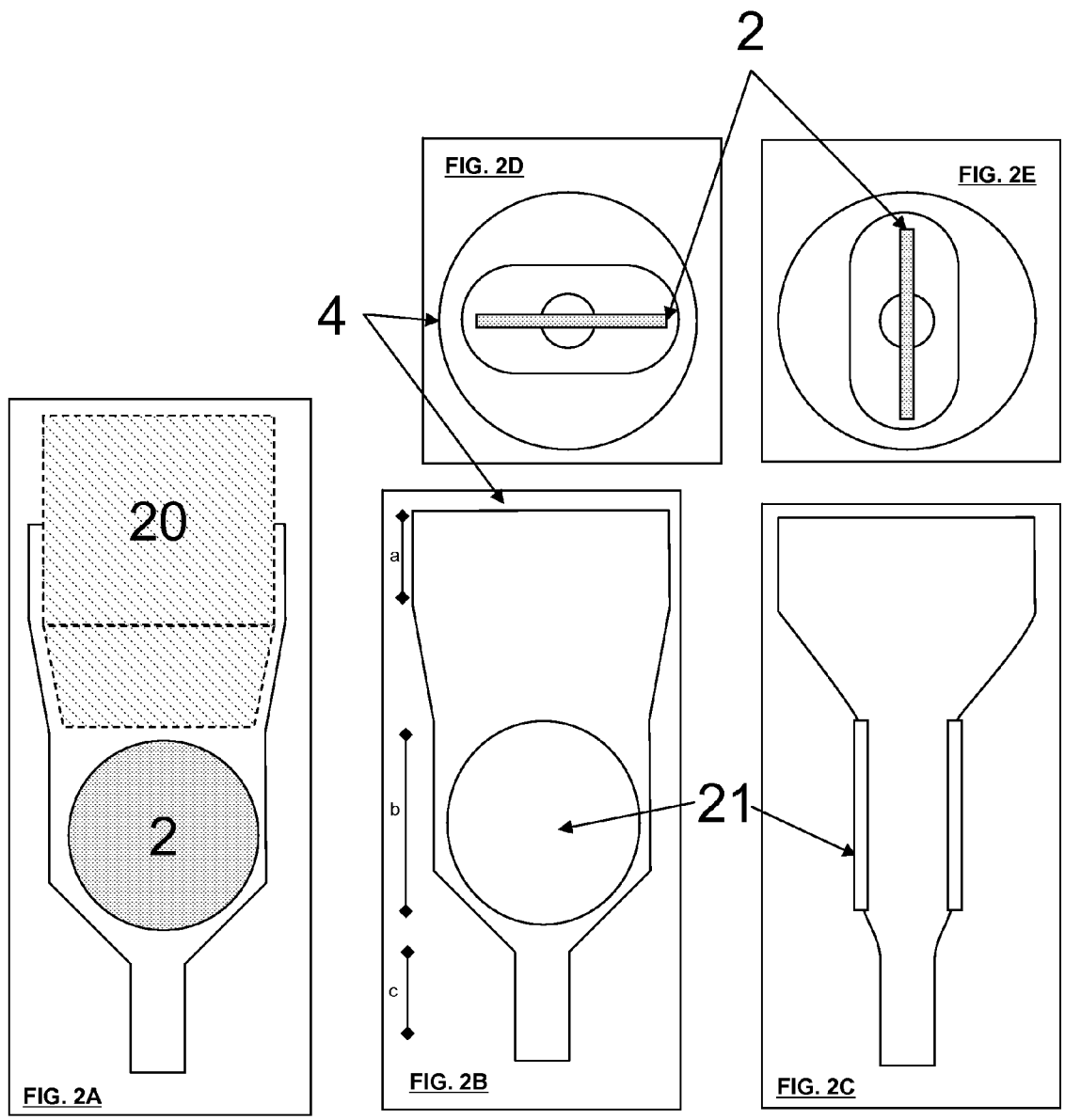
FIGS. 2A-2E are schematic diagrams of one embodiment of a GHMP according to the invention.
Figure 3:
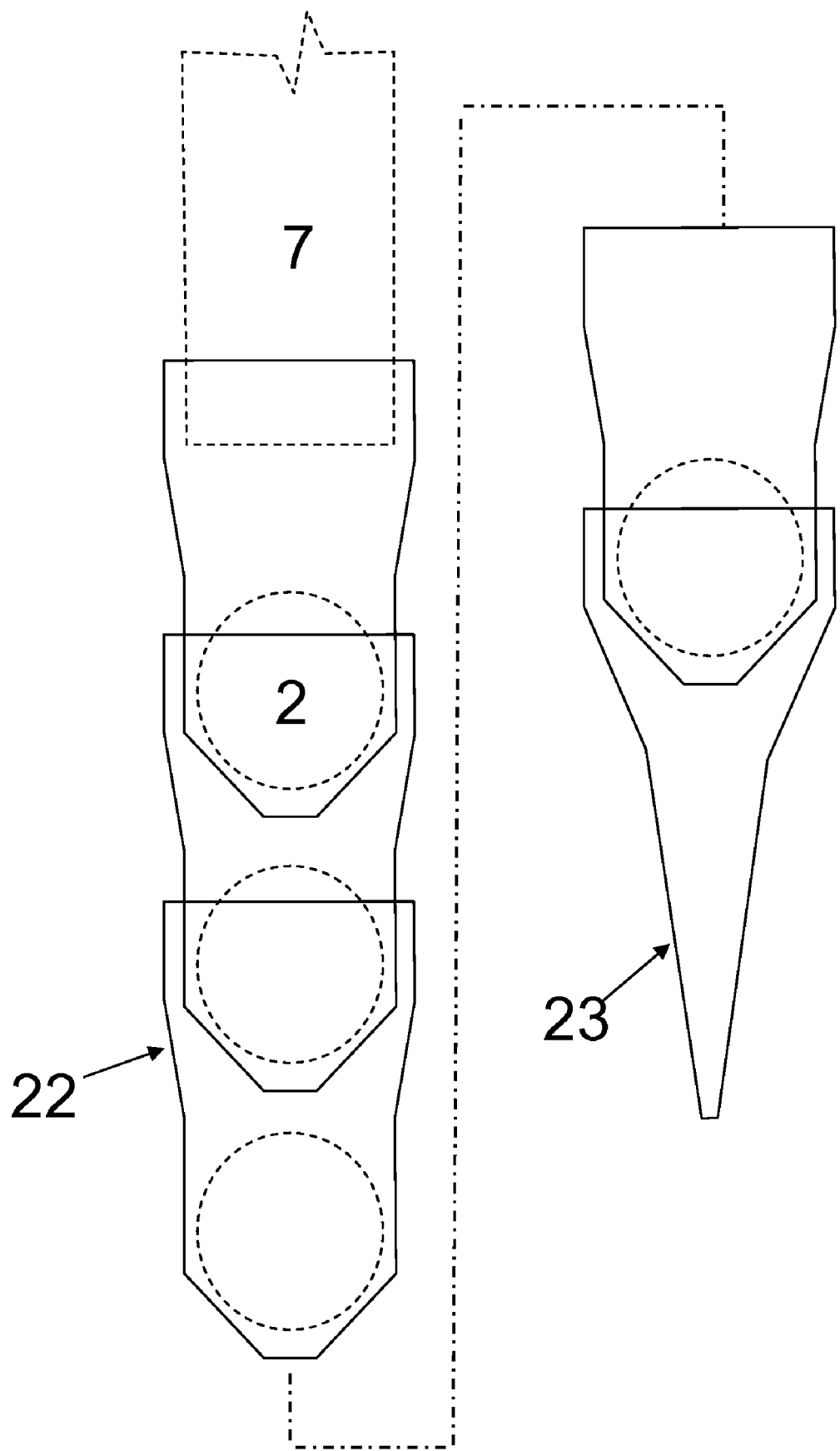
FIG. 3 is a schematic diagram of one embodiment of the invention showing multiple GHMPs stacked together to entrap a specimen on a grid and fitted to a conventional pipette tip.
Figure 5B:
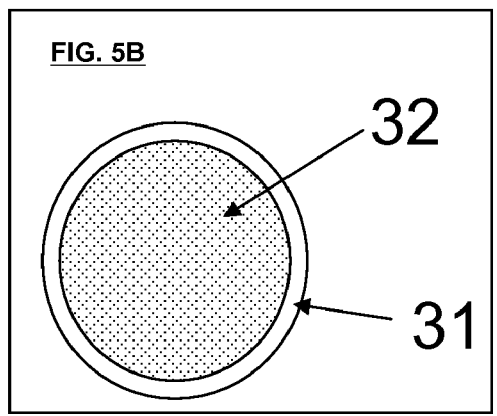
FIGS. 5A-5C are schematic diagrams of another embodiment of the invention showing a specimen holder micropipette device (SHMP).
Figure 5A:
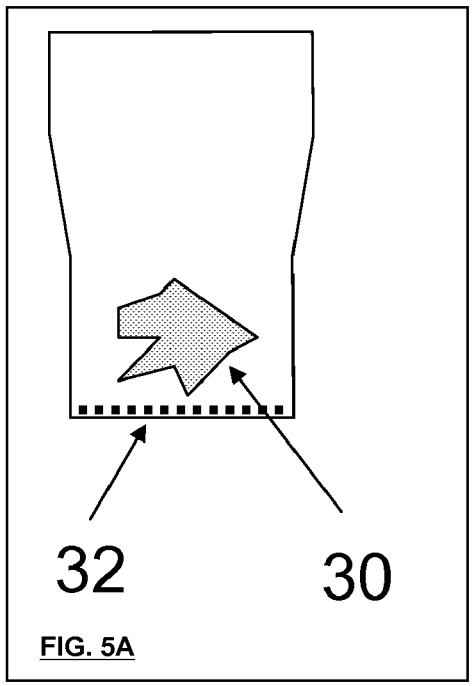
Figure 5C:
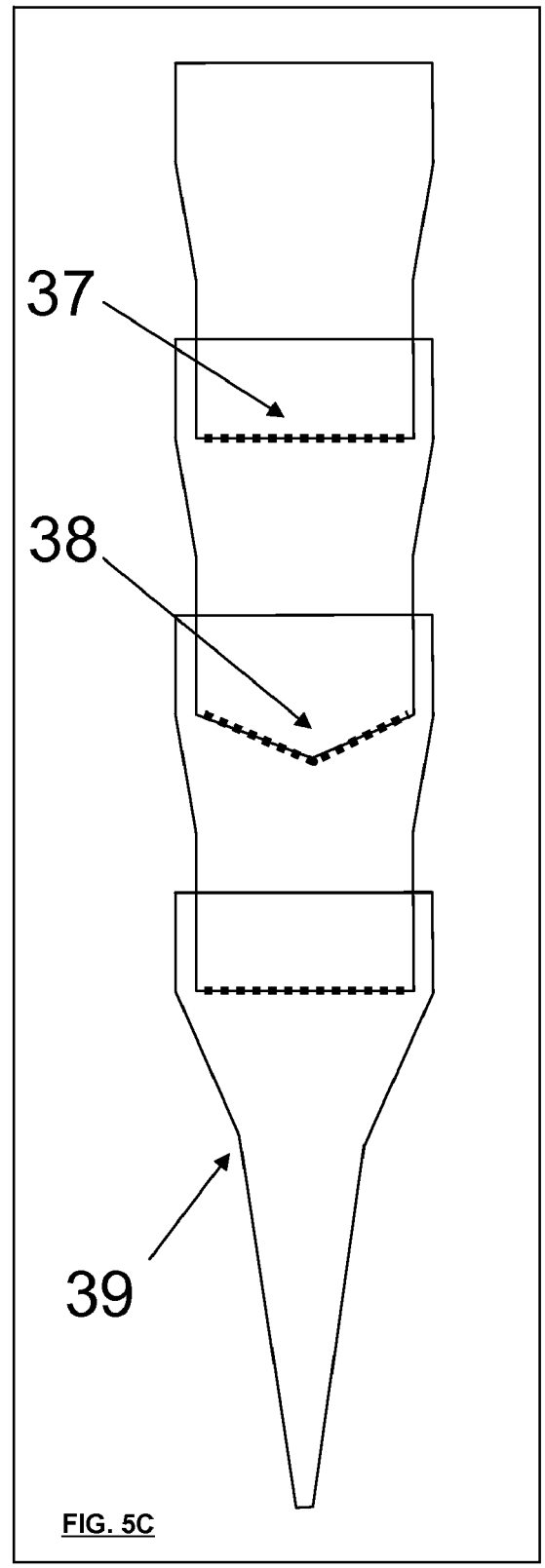

In the embodiment shown in FIGS. 5A-C, each SHMP 37/38 is configured and shaped so that the inside diameter of the upper portion mates to a pipette or other similar device, while the outside diameter of the lower coupling mates with the inside upper portion of additional SHMPs or to pipette tips 39 of the appropriate size. Pipette tips can be used to extend the reach of SHMPs. Further each SHMP is unitarily molded to include a screen or filter comprising a restricted aperture i/o (as shown in FIG. 2, line c, or a plurality of apertures 32 as shown in FIG. 5B.

In various other exemplary embodiments, SHMPs with bottoms that do not have molded-in tips, i.e. that are flat like SHMP 37 or tapered like SHMP 38, reduce the volume of the SHMP (by eliminating the input/output section) reduce the necessary amount of storage space required for SHMP, and facilitate the pipetting of viscous fluids by increasing the cross-sectional area. These SHMP designs also simplify production of the devices since the porous screen or filter element 32 can be produced directly during molding, or secondarily by cutting, drilling, or other processes during manufacture. Wedge-shaped, chisel shaped or tapered bottoms like SHMP 38 or other concave shapes like SHMP 22 (FIG. 3) (concave when viewed from the inside of the SHMP) facilitate specimen positioning within the SHMP, with some tapers further reducing the volume of the SHMP reservoir. Specimens may nestle into the center bottom of the SHMP into the concavity. This design is useful for embedding since the specimen can be manually oriented into the taper or wedge or other shape by direct manipulation (after removing the SHMP from the pipetting device), or the specimen may automatically settle into the bottom of the SHMP. In many applications it is desirable to have the specimen in a particular orientation once embedded. Secondly, having the specimen at the apex of the SHMP and the resulting specimen block will reduce the need for trimming the block prior to sectioning (for TEM or LM or other application), thereby reducing the time and effort necessary to prepare specimens for analysis. SHMPs can also be shaped to accommodate microscope slides, microscope cover slips, and many other materials and substrates that are themselves study objects or may be substrates for study objects for microscopy or other analytical instruments.

Specimens embedded in SHMPs can be directly trimmed and then sectioned without first removing the embedded specimen "block" from the SHMP. Those of skill in the art will appreciate that depending on the shape of the SHMP used e.g., flat shaped, such as 37, wedge/tapered shaped, such as 38 or funnel shaped, such as 31 (FIG. 4), the amount of trimming necessary will vary. Embedded specimens can be removed from the SHMP first, if desired, but since SHMPs can be produced from materials that are readily cut, including plastics, such as polypropylene, polyethylene, polyvinyl chloride, polycarbonate, polyethylene terephthalate and polytetrafluoroethylene, for example, trimming and sectioning can proceed directly without such removal. If the SHMP is labeled as shown in FIG. 8 the label 51 will be retained if the specimen is not removed from the SHMP.

Figure 6A:
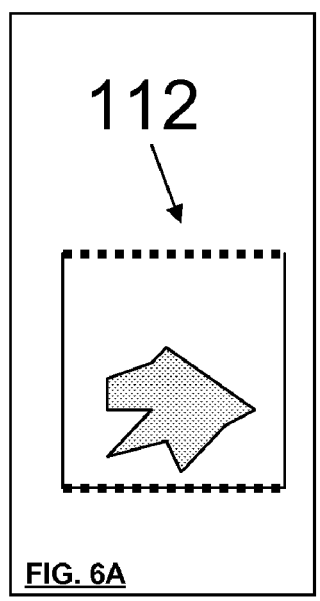
FIGS. 6A-6D are schematic diagrams illustrating an alternative embodiment of the SHMP.
Figure 6C:
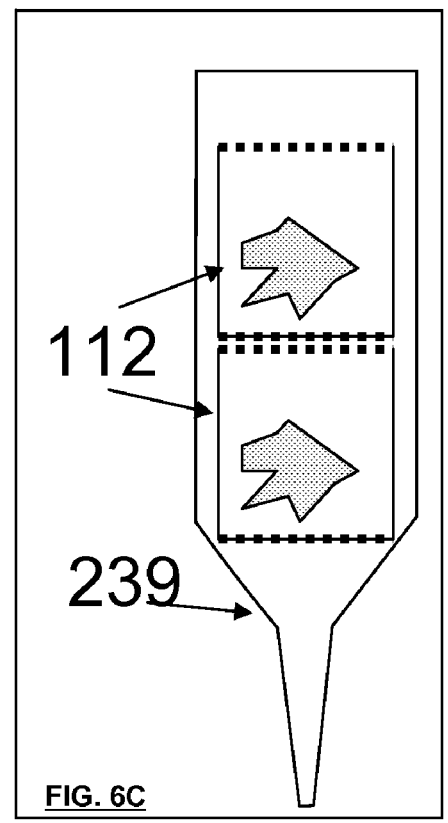
Figure 6B:
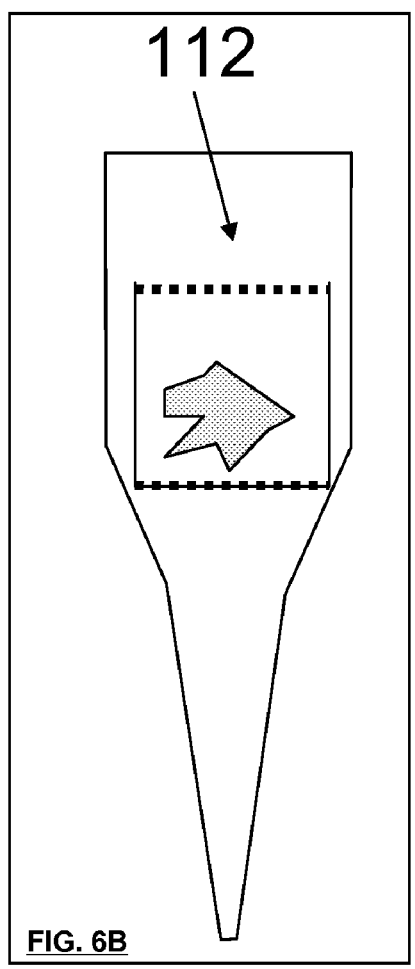
Figure 6D:
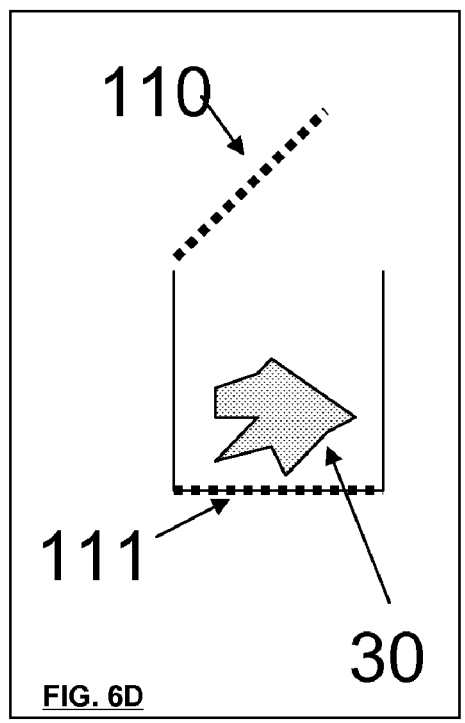

In yet another embodiment, shown in FIGS. 6A-6D, the SHMP 112 or comprises a box-like configuration that can fit into a pipette tip 39. In this embodiment, the SHMP 112 is box or cassette that is inserted into a conventional pipette tip that holds the specimen 30 during fluid exchanges and other processing steps. This type of holder is a specimen holder pipette insert (SHPI). The SHPI 112 will have screen elements on at least the top 110 and bottom 111 to allow fluid exchanges and a means to open and insert the specimen 30 and then close to entrap the specimen 30, such as a hinged snap top 110 as shown in FIG. 6D. The SHPI 112 is then inserted into a pipette tip 39 shown in FIG. 6B. Multiple SHPI 112 units can be inserted into a suitable length pipette 239 as shown in FIG. 6C.

EXAMPLE 2

Preparation of SEM and Similar Specimens

An additional embodiment of the invention is shown in FIGS. 7A-7D. This embodiment is an SHMP 31 in which the screen or filter 40 is comprised of a mechanically robust support produced from an electrically conductive material (such as a suitable metal), or from a material that can be treated to provide electrical conductivity. The screen or filter 40 can be readily removed from the SHMP 31 and is then self-supporting. The screen or filter element 40 is conductive to facilitate use as a specimen support for SEM, but may also be used for other applications such as optical microscopy and atomic force microscopy where conductivity is not required. The pore size of the filter or screen 40 is selected to entrap the study objects as shown in FIG. 7B. As shown in FIG. 7A, a solution (or a suspension or a powder) of small study objects 41 are placed in the SHMP 31 and are then concentrated upon the conductive filter support 40 by filtration resulting in multiple study objects 41 opposed on the filter 40, wherein the SHMP 31 is used as a pipette tip to force fluid out from a pipette to thereby transport the study objects 41 to the filter or screen support 40, shown in FIG. 7B. A fluid introduction apparatus 62, shown in FIG. 10 can introduce additional fluid volumes to enable this transport. Study objects 41 may also be deposited upon the filter 40 by centrifugation wherein the SHMP 31 is placed in a cylindrical holder 43 that supports the SHMP 31 in a centrifuge (not shown) illustrated schematically in FIG. 7C. The cylindrical holder 43 provides a reservoir 44 for the suspending solution that is forced through the filter 40 during centrifugation.

It should be appreciated that some study objects will not require such sedimentation steps but will automatically settle onto the support 40. In this embodiment, the SHMP 31 can be used for any and all desired processing steps in whatever order is selected, such that filtration or centrifugation of the study objects 41 may occur at an early, late, or intermediate step in specimen preparation. FIG. 7D illustrates the robust screen 40 upon which study objects are deposited and can be removed from the micropipette tube and then further prepared for analysis, such as coated with a conductive layer of evaporated metal for SEM. As desired, the specimen 41 may be returned to the SHMP 31 for storage following SEM or TEM imaging. To facilitate repeated examination (and return to the SHMP for additional processing or storage) the filter 40 has a clearly identified upper specimen supporting face 45, and a downward facing face 46. The upper specimen supporting face 45 may be prepared with a grid or "finder" pattern, to enable locating specimen areas of interest. The SHMP 31 may have a variety of sizes and shapes. One useful size and shape is to accommodate screens or filter that are nominally 3 mm in diameter since such sizes allow use in SEMs and TEMs with fittings to hold TEM grids. In some applications, TEM grids can then be used as the filter or screen.

EXAMPLE 3

Positive Identification

It is difficult to mark or specifically identify individual microscope specimens due to their small size. Any identification marking or device would likely be too small to be useful as it would generally not be visible or otherwise identifiable without magnification, such as with a dissection microscope. Moreover, such marking cannot be conveniently done on a grid by a user, at least not without special equipment, nor may a tissue specimen or non-biological specimen be readily marked as most specimens are no more than a few millimeters in size. Current methods for identification during preparation or in storage depend upon the location of the specimen for its identification, such as via a numbered location in a grid box or labeled vial. Since grids are the end stage of TEM specimen preparation and as a single specimen may be sectioned and mounted on dozens of grids, and as such processing may have entailed many days of labor, the logistics of grid identification and management are a considerable problem. Hence, identification of grids is used as an example of how the present invention can simplify the tracking and identification of microscopy specimens. Since grid processing is not done within the grid box, the grid must be removed from the box and returned to the box for each preparative procedure, other processing, and of course for analysis or other examination. With the present invention, one grid can always be kept, processed, and stored within a single GHMP, or one specimen within an SHMP. Thus, once a grid is prepared and inserted into a GHMP it is possible that it may never need to be removed except for examination in an electron microscope or during analysis in other instruments. (As noted above, when desired and appropriate, more than one grid may be held in a single GHMP so designed, or more than one other study object within an SHMP.) This greatly reduces the risk of damage or loss. Thus, a significant benefit of the GHMP/SHMP design in which one specimen or study object (such as a TEM grid) is nearly always within the invention (the GHMP or SHMP), is that the study object can be positively identified and traced by identification of its GHMP or SHMP.

Figure 8A:
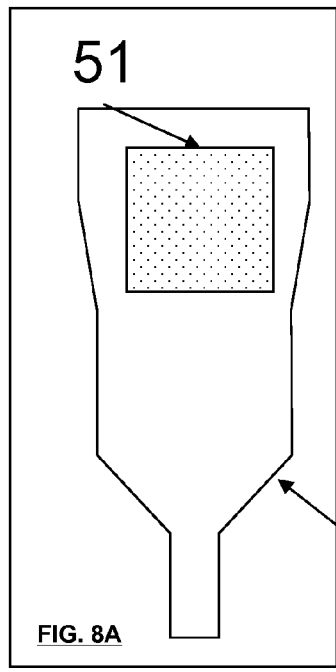
FIGS. 8A-8E are schematic diagram showing various embodiments of the invention in which labels or other forms of identification are placed on the SHMPs or GHMPs.
Figure 8B:
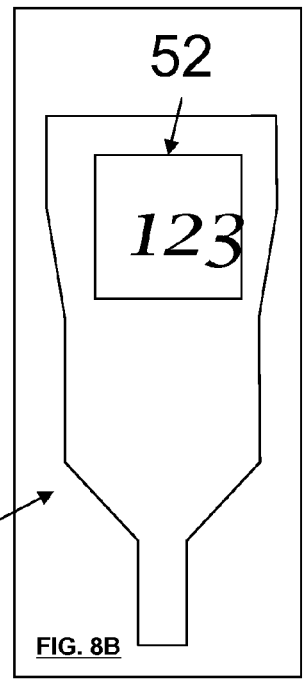
Figure 8C:
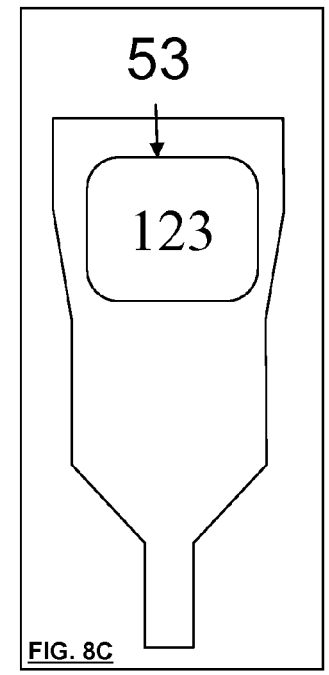
Figure 8D:
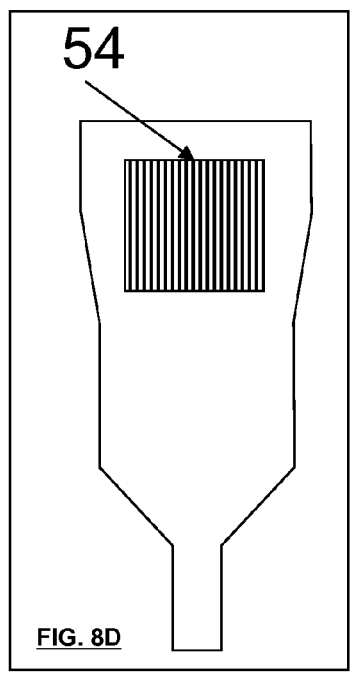
Figure 8E:
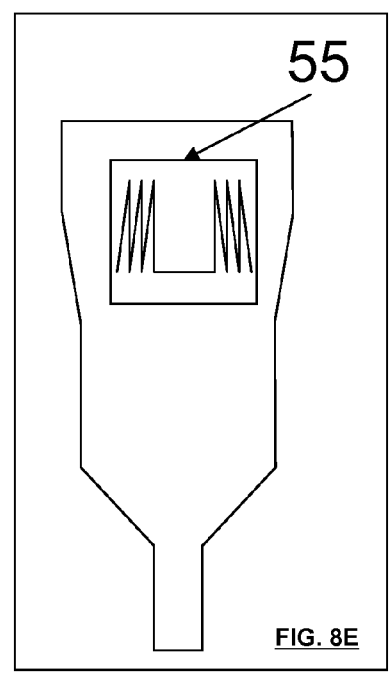

FIGS. 8A-8E illustrate one embodiment where the GHMP/SHMP are positively labeled via various methods. The GHMP/SHMP reservoirs 31 are large enough to readily apply such identification to each unit while sufficiently small and inexpensive to make it feasible to use one holder for each grid (or other specimen, such as with an SHMP), and not so large as to be inconvenient or wasteful for purposes of fixation, storage or archiving. FIG. 8A, shows that such identification can be a number or other mark that is hand-written upon the GHMP/SHMP by the end user upon a region that is treated for such labeling 51, a pre-printed number or mark such as a laser etched or molded-in mark 52, shown in FIG. 8B, a sticker applied to the GHMP/SHMP 53, shown in FIG. 8C, a universal product code (UPC) or other machine readable mark 54 shown in FIG. 8D, or a telemetry readable mark such as a radio frequency identification tag (RFID) 55 shown in FIG. 8E. It will be apparent to those skilled in the art that there are many additional means of identification that are not illustrated but that are within the scope of the present invention including color coding, and molding identification markers or signal producing markers within the GHMP/SHMP units. Thus, the GHMP/SHMP 31 provides improved identification for specimens such as is critical for many applications, for example with clinical pathology specimens, determining the chain of custody for forensic specimens in legal proceedings, and for protocols such as necessary to achieve good manufacturing processes, good laboratory practices, international standard organization (ISO) certifications, and many others.

In various exemplary embodiments, the sample identifier may comprise any conventional device. However, in some embodiments the identifier may be a machine readable device as shown in FIGS. 9A-9C. As shown in this embodiment, machine readable codes can include 2D bar codes 56 of various types, or other machine readable codes. Such machine readable markings may be placed in various locations on specimen holders (SHMP, GHMP, SHPI) to facilitate reading by manual or automated apparatus. For example, as shown in FIG. 9A, the marking can be applied on the SHMP/GHMP/SHPI body 31, upon a flap or protuberance 57 that can be molded onto the SHMP 31. Other places of attachment include a cap 58 as shown in FIG. 9C with the code readable from the top or from the inside of the cap 58 when the cap 58 is open (not shown), as may be required for a given application. Alternatively, machine readable identifiers can be located on the SHMP/GHMP/SHPI underside 59 to enable reading by the appropriate bar code reader or other scanning device 50, from below when SHMPs 31 are closely packed in holders 60 as shown in FIG. 9B.

EXAMPLE 4

Apparatus for Fixation

Figure 10:
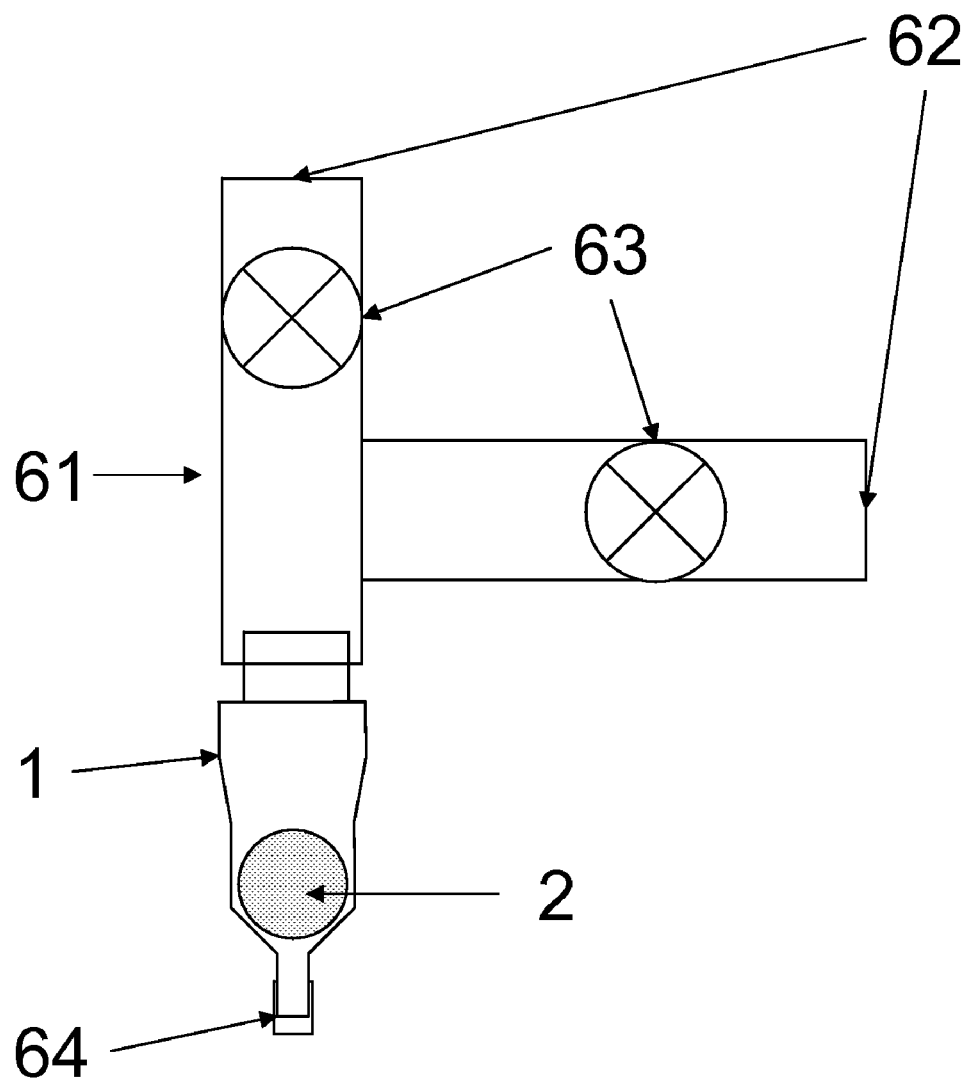
FIG. 10 is a schematic diagram of one embodiment of the invention optimized for fluid exchanges where, even momentarily, it is not desirable to have no fluids present, such as in the preparation of some especially delicate procedures to prepare TEM grids or specimens.

Certain procedures require rapid exchange of fluids such that that the specimen is always or nearly always immersed. One such procedure is specimen dehydration (the removal of water), which is often accomplished by incrementally increasing concentrations of a solvent such as ethanol. Whilst the enclosed nature of the GHMP (or SHMP) greatly slows drying after the first solution is expelled and before the second is introduced, it is possible that inadvertent drying could occur. This addition to the GHMP/SHMP device is shown in FIG. 10. FIG. 10 illustrates embodiments of the invention useful in the simultaneous removal of one fluid via displacement by the second. Thus, the specimens always remain immersed in a fluid. The device is a "Y" tube 61 that allows two separate fluid inlets 62 to be connected to the GHMP 1 containing the grid 2 (or other study object). Each inlet may contain a valve 63 to control opening or closing, or such function may be provided by the connecting device. A cap 64 or a valve may be incorporated at the outflow end of the GHMP 1 for long-term retention of fluids. In various embodiments the "Y" device 61 can also contain a multiplicity of inputs (greater than 2) and can be incorporated into automatic fluid handling system. Thus, specimen processing can also be achieved with SHMP/GHMP using unidirectional flow systems rather than solely displacement pipetting. The "Y" device 61 also enables processing with larger volumes of fluid than can be readily held in the reservoir of a pipette, and enables fluid flow to occur in only one direction, such as to deposit study objects 41 upon a filter or screen 40, as in FIG. 7.

EXAMPLE 5

Simultaneous Fixation of Multiple Specimens

Figure 11:
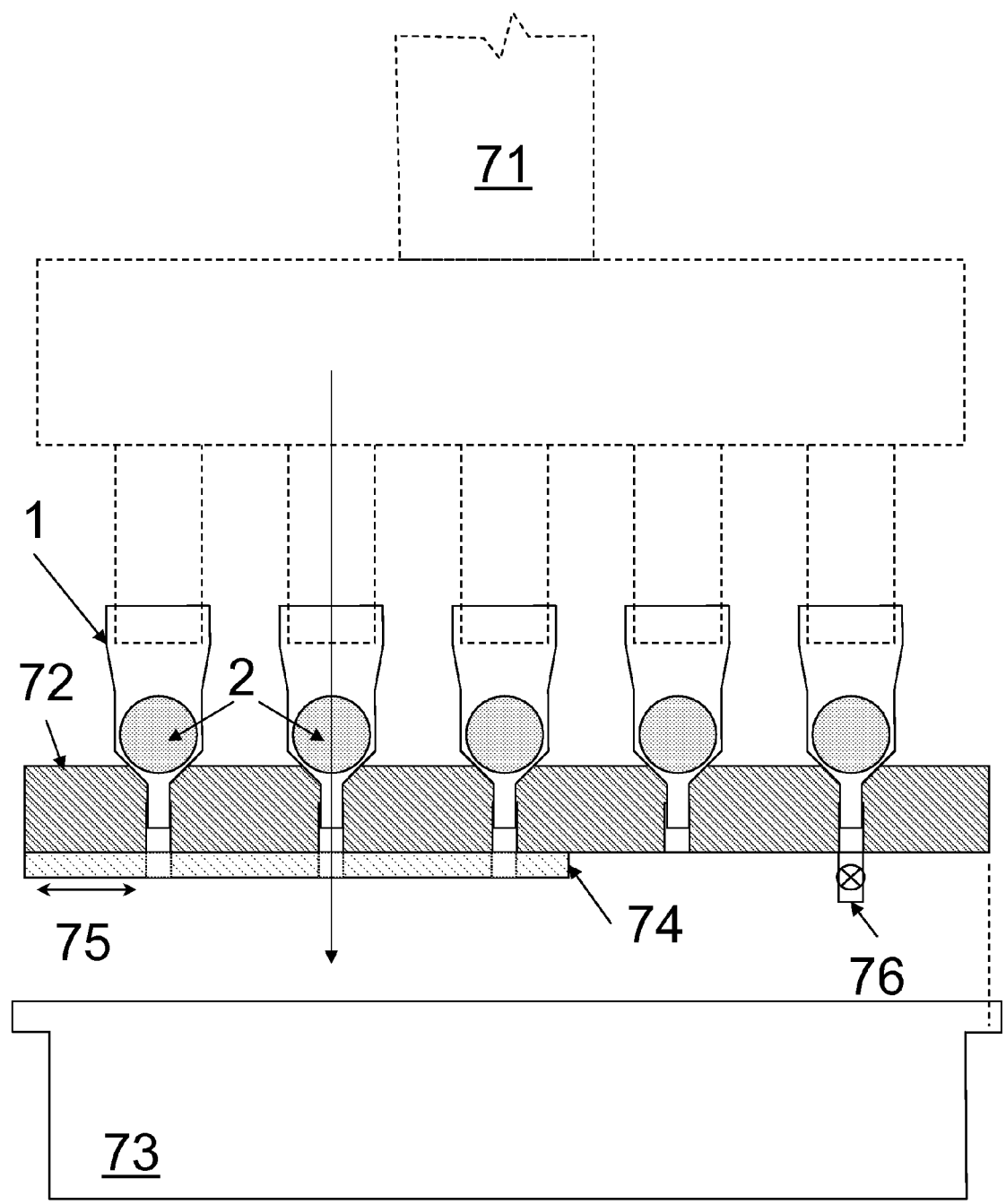
FIG. 11 is a schematic diagram of one embodiment of the invention where the preparation micropipette is optimized for multiple specimen or grid preparation.

FIG. 11 illustrates the simultaneous processing of multiple grids 2 held within multiple GHMPs 1 (or SHMPs). This can be accomplished by processing the specimens/grids 2 in arrays with multiple barreled pipetters 71. Holders 72 for GHMPs may be designed with the same spacing as used in standard multi-well plates so that standard multi-barrel pipettes may be readily used, or in other convenient spacing and arrangement such as to enable the use of automated or robotic fluid delivery systems. Support bases specific for the processing of specimens in GHMPs 1 provide spacing between GHMPs congruent with multiple pipetteing devices or automatic fluid handling systems, provide firm support, and provide a catch basin 73 for rinse waste that, in some embodiments may include a drain. As required, valves 74 can be included to control waste flow from groups of GHMPs 1. In particular embodiments such valves 74 might be actuated by a sliding bar 75 or other means to simultaneously control flow to multiple GHMPs. In alternative embodiments waste flow may be controlled by individual valves 76 associated with single GHMP 1. As shown in FIG. 11, the grouped valve 75 is open. Such valves can be useful where long-term retention of fluid is required.

EXAMPLE 6

Processing in Bundled Groups

Many processing procedures are more readily accomplished by immersion of grouped specimens rather than by pipette flow through one GHMP (or SHMP) at a time. Such procedures may include dehydration by successive immersion in increasing concentrations of ethanol, and other procedures including especially drying by the critical point procedure (which occurs in a high pressure chamber). In these embodiments, the GHMP or SHMP is not being used as a pipette but is rather being used for specimen storage, although its unique pipette character and labeled storage capacity are retained.

Figure 12A:
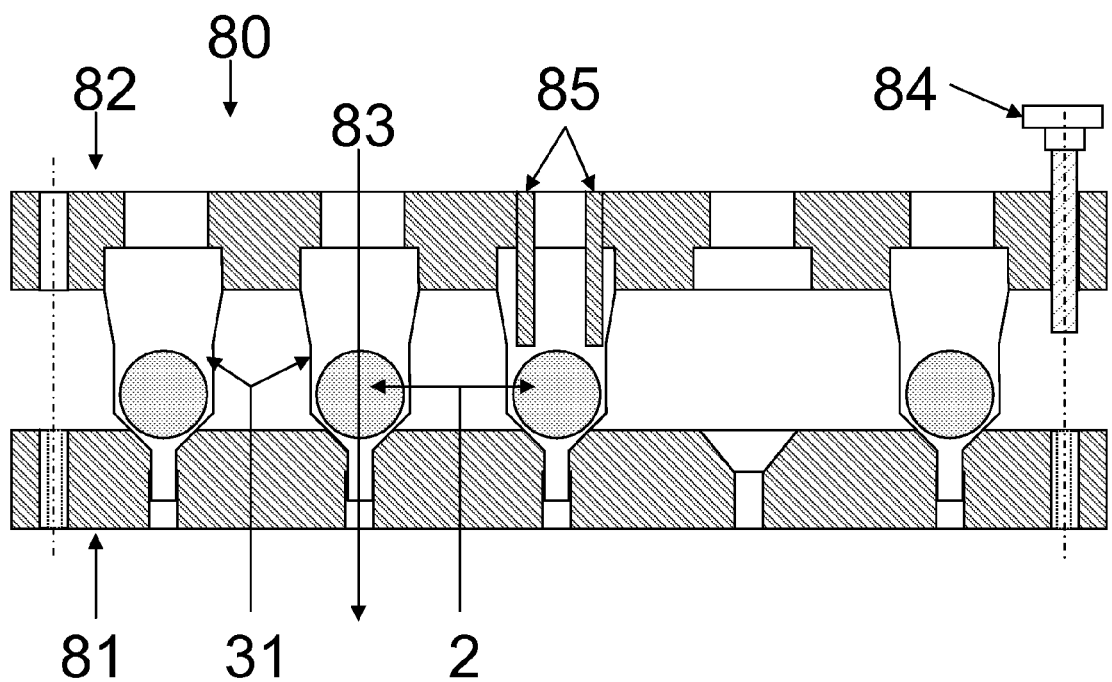
FIGS. 12A and 12B are schematics showing one embodiment of the invention including a holder for multiple micropipette processing devices for bundled preparation.
Figure 12B:
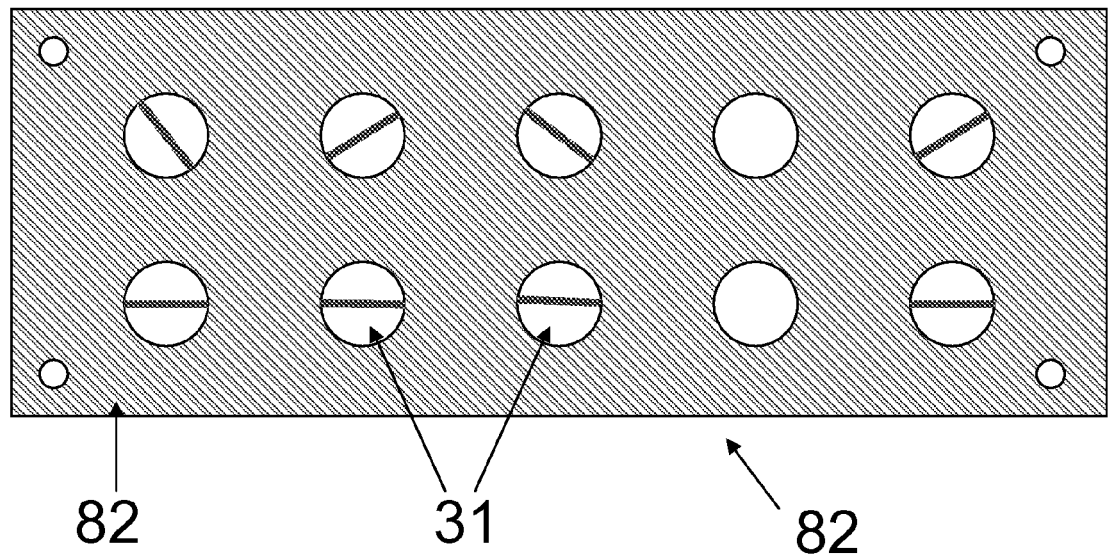

In various exemplary embodiments, the holder 80 for GHMP/SHMP 31 units shown in FIGS. 12A and B is intended for such procedures. FIG. 12A shows a cross-sectional view with four GHMPs 31 containing grids 2, and FIG. 12B shows a top view of the holder 81 with a 2×5 array of GHMPs 31. FIG. 12A shows 4 TEM grids in the same orientation. FIG. 12B shows the TEM grids 2 in various orientations since orientation does not need to be controlled in this embodiment. GHMPs 31 containing TEM grids 2 are placed on a base 81 and are held in place with a top 82 that sandwiches multiple GHMPs 31 together. Free fluid flow is enabled through the base 81 and top 82 of the holder 80 through the bore 83 of the GHMPs 31. The top 82 and bottom 81 are aligned and held together with fasteners such as, for example, thumbscrews 84 or any similar device. In various embodiments, restraints or retention elements for the grids 2 or specimens inside the GHMP/SHMP 31 may be provided by retention members 85. The overall shape of the GHMP/SHMP holder 80 may be rectangular, as shown in FIGS. 12A and 12B, to accommodate pipettes or automatic fluid delivery and to fit certain critical point drying (CPD) chambers (not shown) or other specimen preparation apparatus.

In another exemplary embodiment shown in FIGS. 13A and 13B, the holder 91 may be circular. In this embodiment, the shape of the holder 91 provides a fit amenable to some conventional CPD chambers and round laboratory beakers (not shown). Alternatively, the holder may be prepared in other geometric configurations to fit other devices or accommodate particular spacings or configurations of ancillary equipment such as high-pressure freezers or propane jet freezing apparati. In other embodiments, depending on the application and the type of specimen, certain specimens will require a mechanism to restrain their motion within the GHMP/SHMP 31. FIG. 13B is a side view of FIG. 13A taken along line a-a and illustrating the restraint 85 that may be integral to the holder top 82. Restraint or retention of the specimen can be accomplished with the plug 20 and screens 32 shown in FIG. 2 and FIG. 4. Plugs 20 and/or screens 32 to restrict specimens 2 within the GHMP/SHMP 31 can also be connected to the cap of the holder 80. Such holders 91/80 for multiple GHMP/SHMPs 31 can be used for many different protocols such as, for example, dehydration, rapid freezing, embedding, and others including use within automatic tissue processors and stainers.

EXAMPLE 7

Device for Long Term Storage

Figure 14:
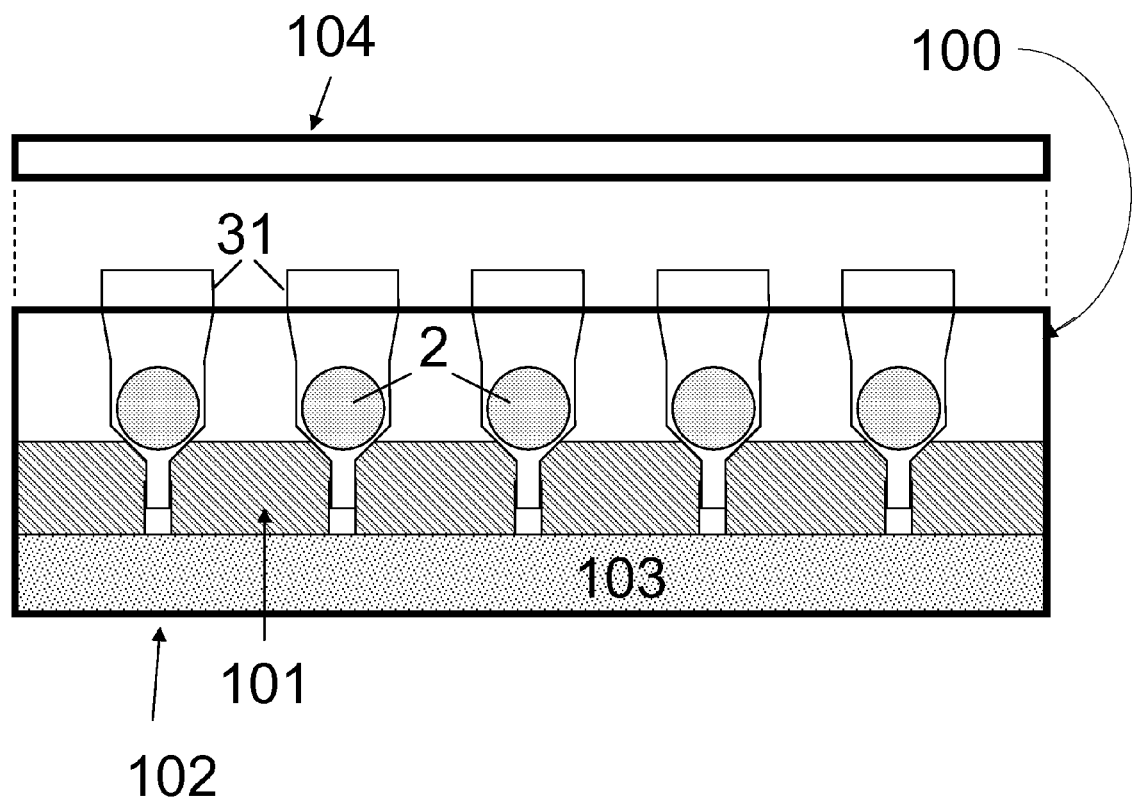
FIG. 14 is a schematic diagram of one embodiment of a storage box used for storing one or more micropipette processing devices.

FIG. 14 illustrates another embodiment of the invention including containers 100 for long term storage of GHMPs and SHMPs 31. As shown, holder 101 for multiple SHMPs, similar to those for use with multiple barreled pipetters 71, as shown in FIG. 11 may be used. In this embodiment, the holders 101 are designed and configured to fit snugly within a container base 102. In some exemplary embodiments, the holder 101 fits within the base 102 so as to provide a space or area 103 for waste, desiccants and/or stains. Further included with the container 100 is a top 104 configured to provide an air-tight seal with the base such that the GHMPs/SHMPs stored within are sealed from the atmosphere. Storage containers 100, such as for archival storage, may use different spacing and positioning to maximize the number of SHMP/GHMPs per unit volume. Typically, holder 101 would be formed of less expensive materials, such as polymers, than those used for processes such as CPD where greater chemical resistance is required for use with solvents under high pressures, and greater density is required to remain immersed in solutions. In these embodiments, the storage container 100 has several features. These include providing a location to insert the holder 100, a space 103 for placing stains (when staining) or desiccants (to keep specimens dry), or to provide other treatments. A tightly fitting cover or lid 104, (e.g. snap-on or hinged) holds the GHMP/SHMPs 31 in place and provide a tight seal, and can also serve to cap each individual GHMP/SHMPs 31 to keep TEM grids 2 or other specimens within. In various exemplary embodiments, storage containers 100 also provide sealed compartments for certain procedures such as chemical vapor staining. Further, it should be appreciated that in various embodiments storage containers can also incorporate features to facilitate reading of labels as shown in FIG. 9.

EXAMPLE 8

Specimen Sectioning

Figure 15A:
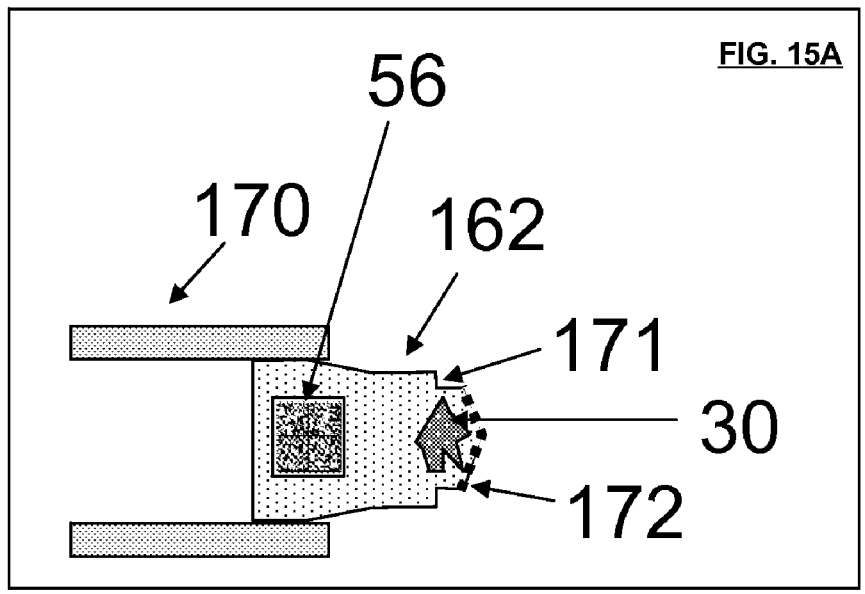
FIGS. 15A-15C are schematics showing one embodiment of the invention illustrating a process of sectioning specimens embedded within SHMPs or GHMP for light or transmission microscopy.
Figure 15B:
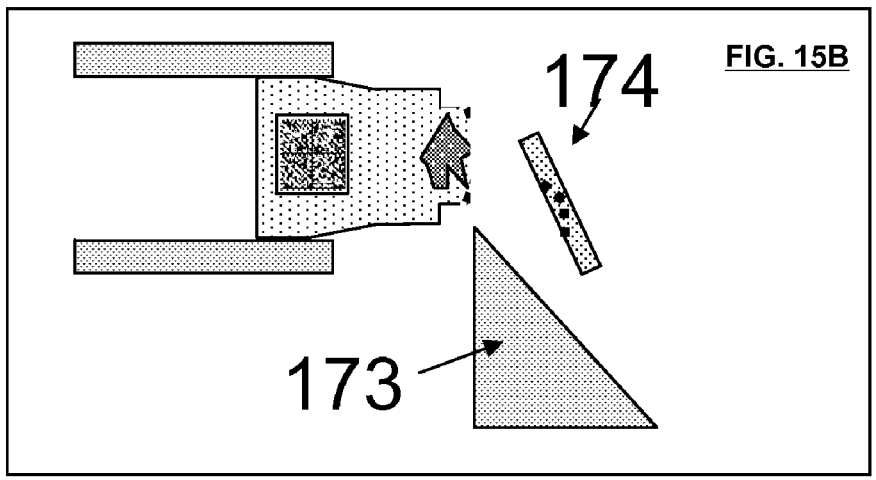
Figure 15C:
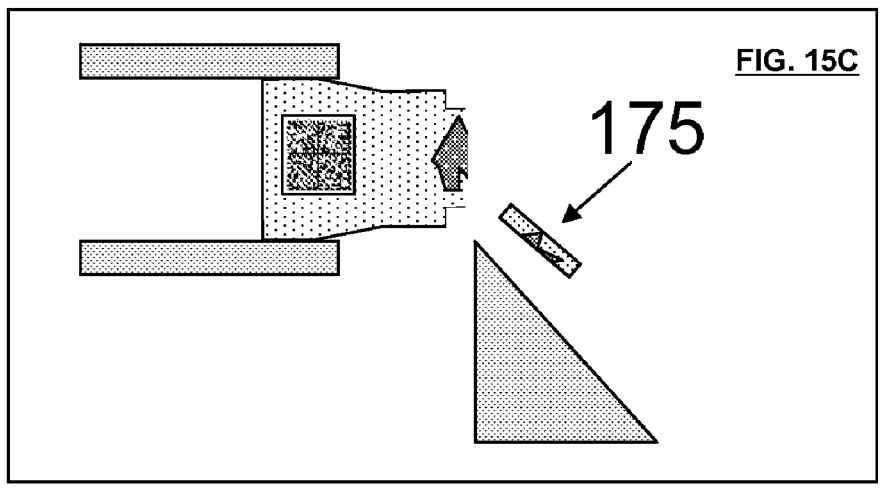

FIGS. 15A-15C illustrate the process of sectioning specimens embedded within SHMP, or GHMP reservoirs for LM or TEM analysis. As shown in FIG. 15A, an SHMP 162 with embedded specimen 30 is clamped into microtome chuck 170. The barcode 56 or other label is retained. The SHMP 162 with embedded specimen 30 is trimmed using a razor or other cutting tool to enable microtome sectioning as shown in FIG. 15B. Trimming can occur right through the SHMP body 171 and the SHMP screen 172 (in various embodiments, these are molded from sufficiently soft materials). The embedded specimen 30 is then sectioned with the microtome 173 (or ultra-microtome) with a glass, metal, diamond or other cutting edge or knife. Initial sections may include the screen 174 and possibly pieces of the SHMP body 162 (shown in FIG. 15B), while subsequent sections will primarily include the specimen 175 as shown in FIG. 15C. The present invention enables and improves the processing of specimens for TEM, SEM and many other types of analytical instruments that are prepared with liquid processing protocols (e.g. staining), resin processing including polymeric embedding, as well as less common vapor phase processing protocols, and secondary instrument based procedures such as critical point drying protocols. Almost any known protocol for biological and non-biological specimen preparation for TEM, LM and many protocols for SEM and many other instruments can be readily accommodated, and be more easily performed with the current invention. The system is also extremely adaptable; hence procedures developed for specimen preparation in the future will also likely also be adaptable for use with this invention. Moreover, since all or almost all processing steps occur within a single capsule (the GHMP or SHMP), the chance of loss, damage or miss-identification is greatly reduced over any other known methodology. To further demonstrate the capabilities of this invention, some additional features, aspects and benefits are discussed below to illustrate the flexibility and utility of the invention.

EXAMPLE 9

System Mat for Sample Sealing

Figure 16A:
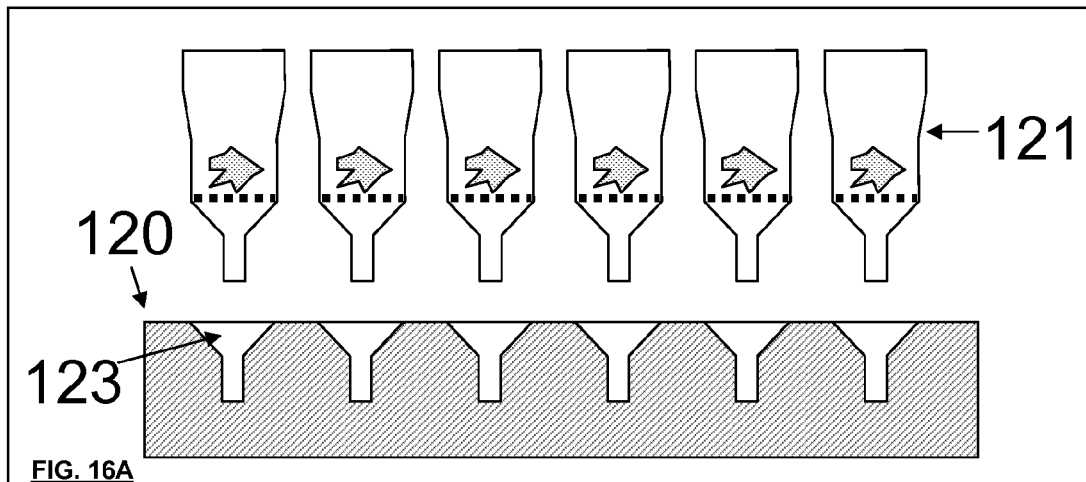
FIG. 16A-16C are schematic diagrams showing one embodiment of the invention illustrating the compatibility of various SHMPs and GHMPs and pipettes with SHPIs with a base for specimen processing or extended storage.
Figure 16B:
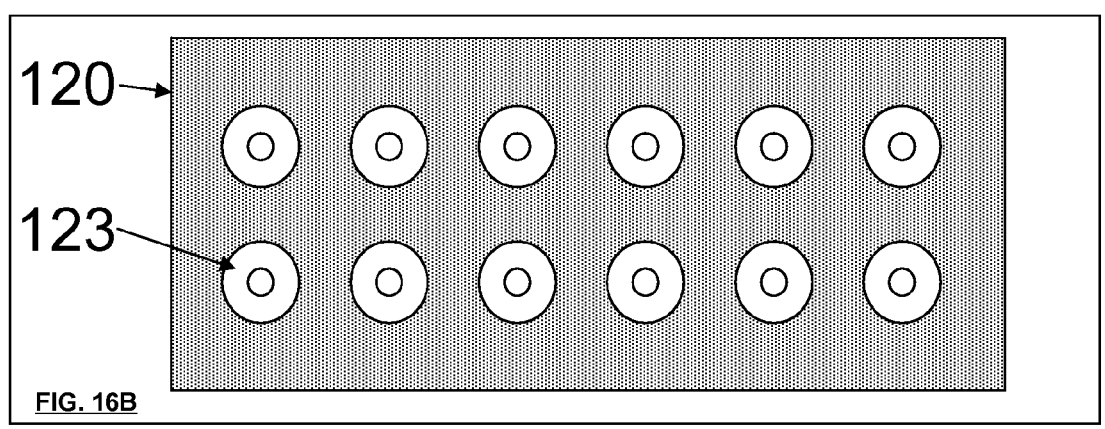

During many specimen processing protocols it is likely that a means may be required to maintain material in the various specimen holders described herein for some extended period of time when it is not desirable or possible to maintain connection to a pipetting device. Examples include when there is a long incubation time with a stain, or during a long fixation step, or when processing is improved when performed in a microwave oven, or during thermally cured polymerization of an embodiment in a conventional oven. The device shown in FIG. 16A is such a shaped mat 120, produced from a material that will provide the necessary quality of seal to hold liquids in the pipettes or holders, and that can withstand the conditions to which it will be subjected, such as microwave irradiation, heating, and chemical resistance. It should be appreciated that in various embodiments, a suitable material will vary depending on the exact conditions, however, in many embodiments such materials will include silicone rubbers, suitable polyurethanes, other elastomers, and some non-elastomers may be generally suitable. A cross-section through a mat 120 intended to hold SHMPs 121. A top view of the mat 120 shown in FIG. 16A illustrates cavities 123 in a 6×2 array in the mat 120 intended to hold 12 SHMPs 121. The spacing between the cavities 123 can be designed to accommodate the spacing in multi-channel pipetters and/or with automatic processing liquid handling systems as shown in FIG. 16B.

Figure 16C:
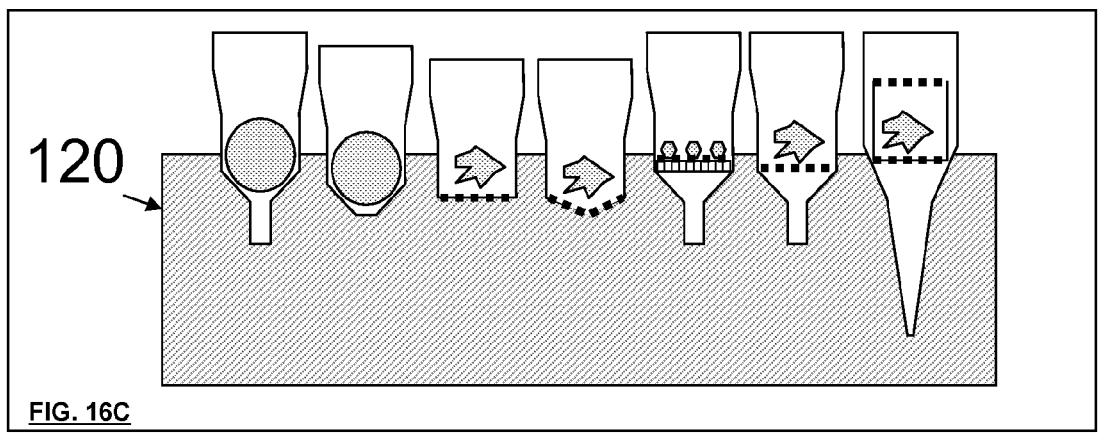

FIG. 16C shows that, in some embodiments, the mat 120 may have different shape cavities 123 for each of the variety of GHMP/SHMP used. Cavities 123 of the proper shape can be produced in any configuration desired for each of the various types of SHMPs, GHMPs, conventional pipette tips with inserted SHPI described herein, as well as for other specimen holders that will also be apparent to those skilled in the art.

The mat 120 can serve other useful functions. SHMPs 121 can be placed in the mat 120 to facilitate initial insertion of specimens into SHMPs. The SHMPs 121 can be filled with buffer or fixative at this stage to keep specimens wet or to initiate fixation. As processing nears completion for protocols where specimens are embedded for sectioning, the mat 120 can serve additional purposes. The open top of the filled SHMPs 121 enables specimens to be physically manipulated into a desired orientation prior to final embedding. Since the last embedding media placed in the SHMPs may be very viscous, rather than introduce the embedding media via pipetting as performed for other fluid exchanges, the embedding media may be delivered from the top via pouring or via another pipette. The mat 120 can then be inserted into the curing oven.

EXAMPLE 10

System for Remote Preparation of Sample

Specimen preparation is often performed away from the laboratory facilities required for complete specimen preparation for light or electron microscopy examination. Such locations include small hospitals or clinics where a physician may obtain a biopsy from a patient. At such locations the collected biopsy is then sent to a facility where its preparation can be completed prior to histopathologic examination. At such locations, a convenient means to initiate the fixation would be desirable. FIG. 17 illustrates such a system intended for use with SHMP devices, or similar devices.

As shown in FIG. 17A, the specimen 130 is obtained and inserted in the SHMP 131 and then capped 132 as shown in FIG. 17B. The capped SHMP is then placed in vial 133, shown in FIG. 17C. The vial 133 can then be connected to a filling apparatus 134 that fills the vial 133 from a reservoir or ampoule 135 of fixative as shown in FIG. 17D/E. The filling apparatus 134 is then removed and a cap 136 is placed on the vial shown in FIG. 17F. The vial 133 can then be labeled and sent to the appropriate facility for specimen preparation and analysis. Alternatively, the filling apparatus 134 could, directly connect to the SHMP 131 for filling. However, a separate vial 133 to hold the filled SHMP 131 is desired since it will protect the SHMP during transfer to the laboratory facility for subsequent processing. Such fixation protocols generally use toxic fixatives, thus, when field use is necessary, the invention according to this embodiment provides a safe and easy method of handling such agents. In an alternative embodiment, the vial filling apparatus 134 remains attached to the vial 133 until delivery to the specimen preparation lab. Once received at the specimen preparation lab the SHMP is removed from the vial and processed as, for example shown in FIGS. 15A-C.

EXAMPLE 11

Handling of Large Specimens

Figures 18, 19:
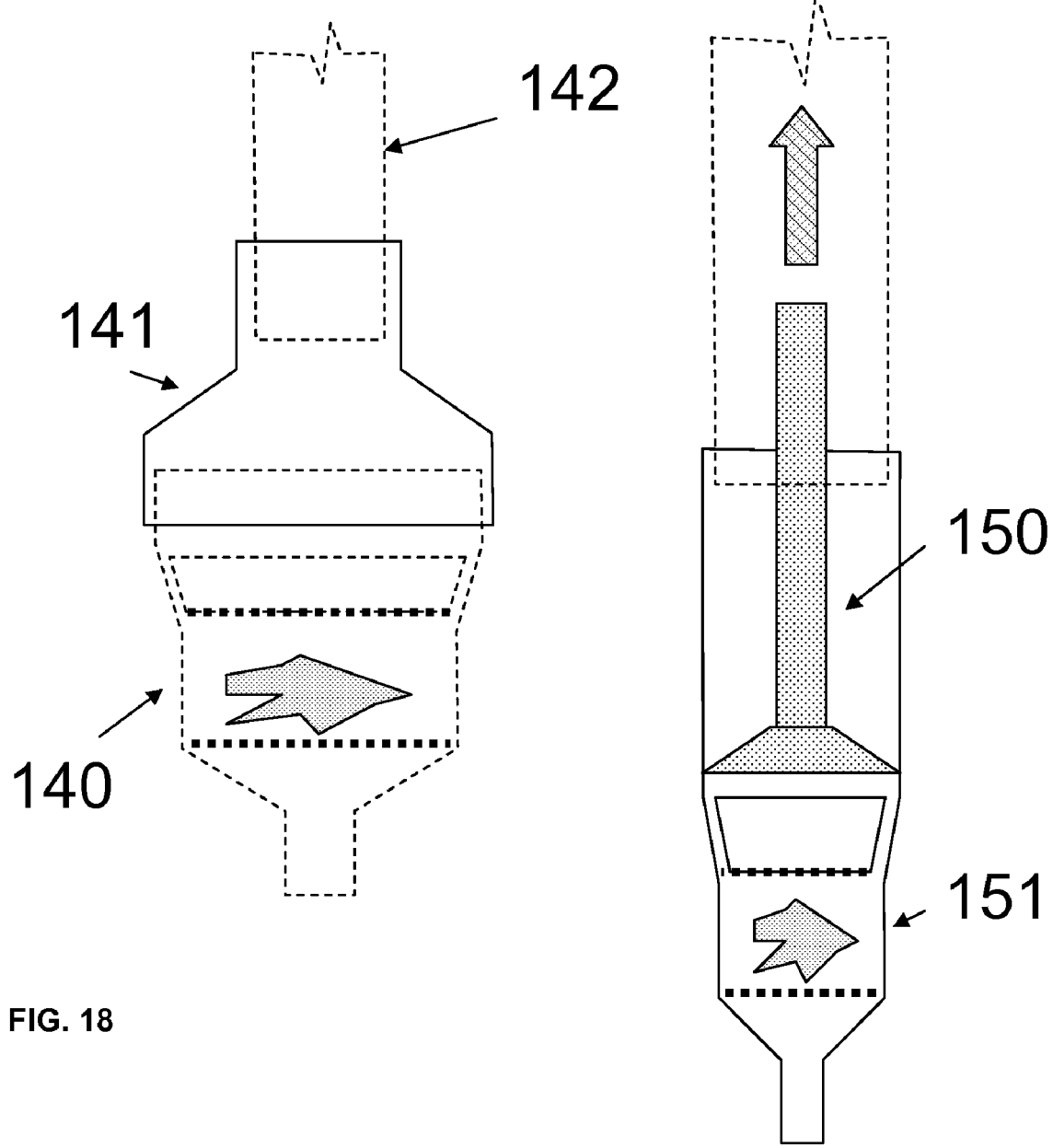
FIG. 18 is a schematic diagram showing the use of one embodiment of the invention for use with extra large specimens.
FIG. 19 is a schematic diagram showing the use of one embodiment of the invention when fixed or processed with viscous fluids.

FIG. 18 illustrates embodiments of the invention useful for handling extra large specimens. Specimens larger than the diameter of standard micropipetters can be accommodated with large SHMPs 140 that are coupled to adaptors 141 that fit the SHMP 140 and the pipetter 142. In this embodiment, the volume of the SHMP and the adaptor may be no more than the displacement volume of the pipetting apparatus.

FIG. 19 illustrates an embodiment of the invention useful for preparing specimens 31 with viscous reagents. In this embodiment, a piston actuator 150 exerts suction displacement forces closer to the specimen 31 to enable a more forceful draw of viscous fluids into the chamber of the SHMP 151.

EXAMPLE 12

Continuous Documentation of Samples

Figure 20A:
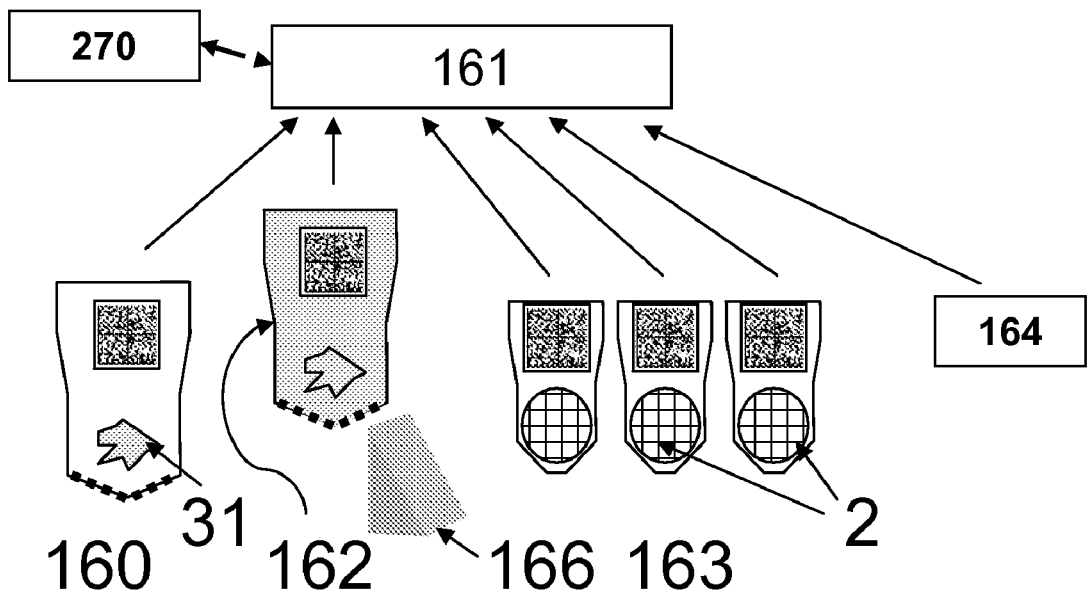
FIGS. 20A and 20B are schematic diagrams showing the use of different embodiments of the invention in preparation of samples for use in transmission electron microscopy (FIG. 20A) and light microscopy (FIG. 20B).
Figure 20B:
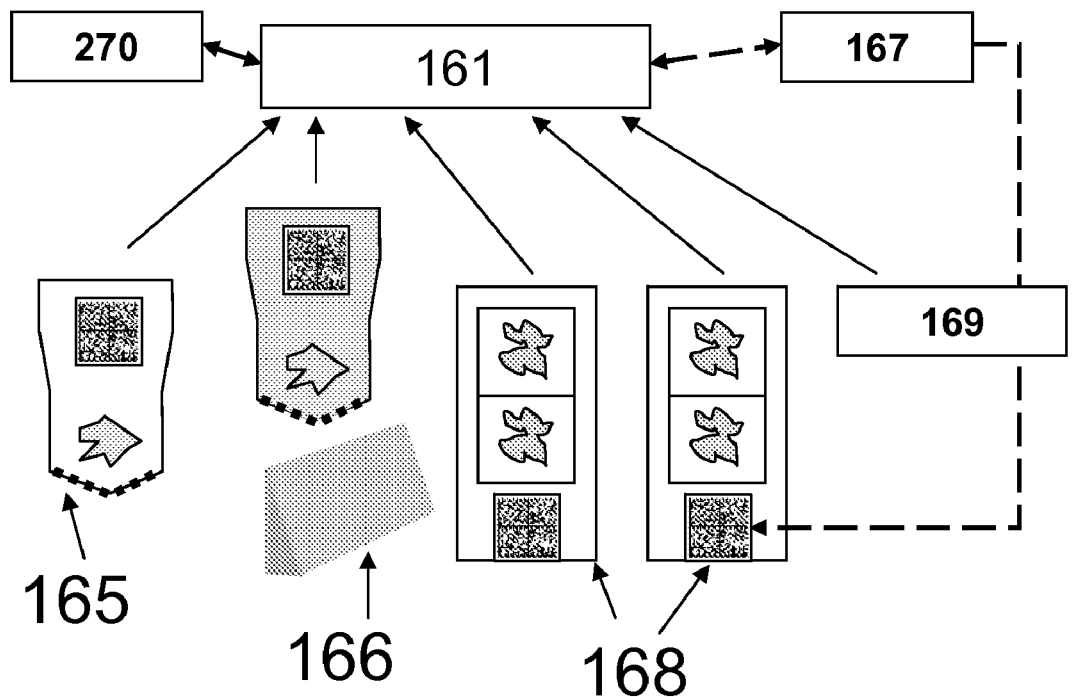

Continuous documentation and tracking of specimens from point of collection through point of analysis is one benefit of the devices and system disclosed herein. Machine readable labeling offers automatic tracking, although substantial benefits can be obtained from text labeling as well. FIGS. 20A and B illustrate an implementation of automatic tracking of specimens using machine readable barcode labeling of specimens implemented with a Laboratory Information Management System (LIMS) 161 when preparing either an electron microscopy sample (FIG. 20A) or a light microscopy sample (FIG. 20B). Those of skill in the art will appreciate that the same principles can also be applied to SEM samples and for other specimens prepared using SHMPs and/or GHMPs.

FIG. 20A illustrates the preparation of a TEM sample. A TEM specimen 31 is inserted into barcode-labeled SHMP 160. The barcode is then scanned into the LIMS database 161 to transfer the details of the specimen 31 to the LIMS database 161 as represented by the arrows. The SHMP 160 is used to prepare the specimen 31 following instructions entered into the LIMS database 161 for each particular specimen. Control is either indirect by providing digital instruction for a technician to follow via a user interface 270, or direct where the instructions control an automatic specimen processing apparatus (not shown). After completion of embedding, the fixed SHMP block 162 is then sectioned with an ultramicrotome. As grids 2 are prepared, these are then inserted into bar code labeled GHMPS 163. Bar code-labeled GHMPs 163 can then be scanned into the LIMS database 161 and linked to the file of the GHMP 160 uploaded at 161. The grids 2 are then processed with barcode scanning used to control the protocol via instructions or by direct machine control. After processing, the grids then remain in the GHMPS for archival storage. The GHMP 163 is scanned whenever the specimen grids contained therein are examined with the TEM 164, with the resulting images further linked to the LIMS database 161.

FIG. 20B illustrates the preparation of a light microscopy sample. A light microscope specimen is handled in a similar manner as the TEM specimen. The specimen 31 is inserted into a barcode-labeled SHMP 165, and the barcode is then scanned into the LIMS database 161 uploading details of the specimen via the user interface 270. The SHMP 165 is used to prepare the specimen 31 following instructions entered into the LIMS database 161 for each particular specimen. After completion of embedding, the fixed SHMP block 162 is then sectioned 166 with a microtome. For LM microscopy, sections are placed on light microscope slides 168 that are printed with barcodes from barcode printer 167 (from the LIMS 161 or printed or labeled by other means to ensure that the barcode is linked to the LIMS record). The barcode labeled slides 168 are then further processed with barcode scanning which, in various embodiments provides automatic download of the staining and other processing protocols to be used. The barcode is then scanned whenever the slides 168 are examined with the LM 169, with the resulting images further linked to the LIMS database 161.

EXAMPLE 13

Examplary Preparation of TEM Sample

Figure 21:
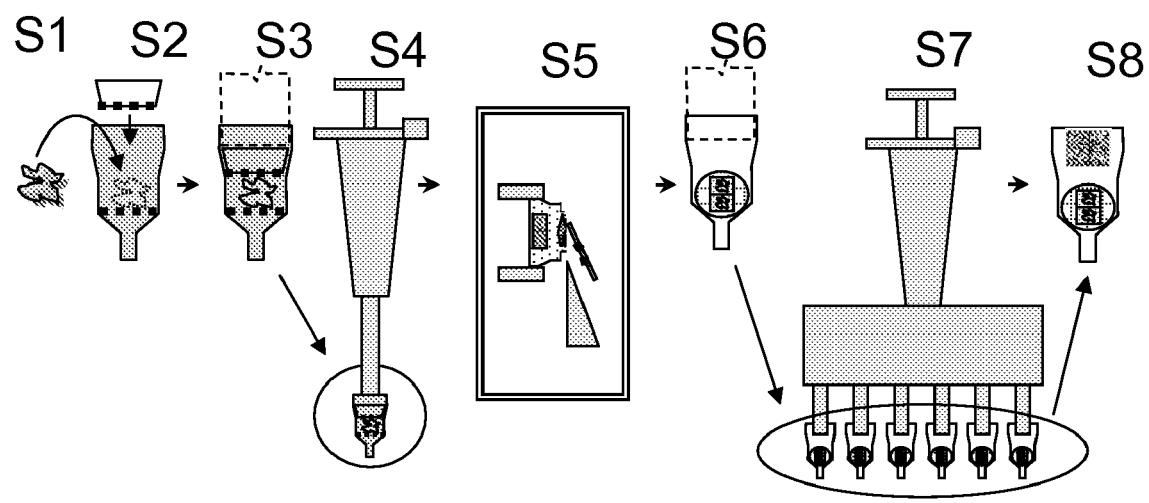
FIG. 21 is a schematic diagram illustrating one embodiment of the invention providing a system of preparing samples for microscopic analysis and storage.

FIG. 21 illustrates one procedure for preparing TEM samples according to the invention. As illustrated, in step S1, the specimen is inserted into SHMP and in step S2 the SHMP is capped. Next, in step S3, the pipetter connected to the SHMP. (In the embodiment shown a single tip pipette apparatus is used). Then, in step S4, the pipetter is used to treat the specimen with typically many tens of fluid exchanges to effect fixation, staining and embedding. In step S5, the sections are cut on microtome and TEM grids are prepared. In step S6 the grids are inserted into a GHMP and connected to a pipetter. (In the embodiment shown in step S7 a multiple tip pipetter is used.) The grids are then further processed through multiple fluid exchanges. In step S8, the fully prepared grid is stored in the GHMP. In the embodiment shown the GHMP is labeled with a bar code. It should be appreciated that in various exemplary embodiments, fully automatic pipette-like apparatus can also be used not (shown) according to the need or desire of the user.

The present invention enables and improves the processing of specimens for TEM, SEM and many other types of analytical instruments that are prepared with liquid processing protocols (e.g. staining), resin processing including polymeric embedding, as well as less common vapor phase processing protocols, and secondary instrument based procedures such as critical point drying protocols. Almost any known protocols for biological and non-biological specimen preparation for LM and TEM, and many protocols for SEM and many other instruments can be readily accommodated, and be more easily performed with the current invention. The system is also extremely adaptable; hence procedures developed for specimen preparation in the future will also likely also be adaptable for use with this invention. Moreover, since all or almost all processing steps occur within a single capsule (the GHMP or SHMP), the chance of loss, damage or miss-identification is greatly reduced over any other known methodology.

To further demonstrate the utility of this invention, some additional features, aspects and benefits are discussed below to illustrate the flexibility and utility of the invention.

Cryogenic Procedures

The GHMP or SHMP can be used for most cryogenic processing protocols including cryo-freezing, cryo-staining, freeze substitution, high-pressure freezing, and long term cryo-storage. Grids can be placed in a GHMP, or other specimens may be placed in an SHMP, and then rapidly frozen in a propane jet (or other cryogens) with a nozzle or group of nozzles directed into the GHMP/SHMP units. Holders such as those shown in FIGS. 12A and B and 13 can be used to support the GHMP/SHMP units with dimensions appropriately modified to fit such devices. Similarly, high pressure freezing may also be accomplished with a holder to support the GHMP/SHMP units in the proper orientation to enable rapid filling with high-pressure cryogen. Rapid freezing can be accomplished by plunge immersion into liquid ethane, liquid nitrogen ($LN_2$) slush or other cryogen using a holder that directs the cryogen directly into the lumen of the GHMP. Since the GHMP/SHMP are small, provide excellent flow through their lumen, and are of low thermal mass materials, the necessary rapid cooling of the specimens within is achieved. Once the study object is frozen, subsequent processing may be accomplished within the GHMP/SHMP including freeze substitution, cryogenic fixation, cryogenic labeling, and cryogenic staining without removal of the study object unit. High thermal mass holders for GHMPs (e.g. metallic such as those shown in FIGS. 12A and B and 13) facilitate transfer from one location to another without specimen warming. Such holders are sufficiently high density to remain submerged under cryogens such as LN2.

Deleterious, Damaging and Toxic Protocols

GHMPs and SHMPs are fabricated from inexpensive polymers (such as polyethylene or polypropylene) that can withstand most treatments without damage, or the GHMP/SHMP can be prepared with more expensive polymers such as polytetraflouroethylene or other materials if greater chemical resistance is required. As the small individual GHMP/SHMP units are inexpensive and disposable they can be used for toxic and potentially damaging procedures that cause permanent staining or damage (e.g. $OsO_4$ and $RuO_4$) without concern. Such staining, in fact, provides a label that such processing was done. With expensive holders, one may not wish to permanently stain a device that will be used for other specimens. However, with the GHMP/SHMP the unit will not be used for other specimens. Additionally, many processes and reagents used for specimen preparation are toxic, radioactive, or are otherwise noxious. Once used, the GHMP can be appropriately treated (e.g. sterilized, autoclaved), neutralized, and discarded (possibly as toxic waste) without cost concerns.

Reduction of Reagents

Each GHMP/SHMP has a very small internal volume thus reducing the amount of material needed to accomplish processing. This is important with expensive reagents such as many biochemical (e.g. antibody) labels and toxic materials.

Reduction of Contamination

Since each study object is processed in its own vial (SHMP or GHMP) this greatly minimizes the potential for cross-contamination from one specimen to the next.

While this invention has been described in conjunction with the various exemplary embodiments outlined above, various alternatives, modifications, variations, improvements and/or substantial equivalents, whether known or that are or may be presently unforeseen, may become apparent to those having at least ordinary skill in the art. Accordingly, the exemplary embodiments according to this invention, as set forth above, are intended to be illustrative, not limiting. Various changes may be made without departing from the spirit and scope of the invention. Therefore, the invention is intended to embrace all known or later-developed alternatives, modifications, variations, improvements, and/or substantial equivalents of these exemplary embodiments.

What is claimed is:

1. A device for preparing microscopy specimens comprising:
   a unitary reservoir, the reservoir comprising;
   a) a first end adapted and configured to accept a pipette and a second end having an inlet/outlet therein;
   b) a screen provided in the second end;
   the reservoir being dimensioned and configured to mate with a second reservoir such that the first end of the first reservoir forms a liquid tight seal with the second end of a second reservoir; and
   the second end of the reservoir being dimensioned and configured to mate with a pipette tip; and
   the reservoir being adapted to contain a specimen for microscopic evaluation and displacement of the pipette results in filling or emptying of the reservoir with one or more reagents;
   whereby filling the reservoir with the one or more reagents prepares the sample for microscopy.

2. The device of claim 1, wherein the screen comprises a plurality of holes.

3. The device of claim 1, further including a replaceable cap for the first end.

4. The device of claim 1, further including a replaceable cap for the second end.

5. The device of claim 1, further comprising a protrusion on an inner face of the reservoir optimized to break surface tension of a liquid contained in the reservoir.

6. The device of claim 1, wherein the reservoir is adapted and configured to accept one or more grids.

7. The device of claim 6, wherein the one or more grids have a specimen for analysis affixed thereto.

8. The device of claim 1, wherein the specimen is prepared, fixed and stored for microscopic analysis within the reservoir.

9. The device of claim 8, wherein after the specimen is fixed, the reservoir and specimen contained therein can be sectioned by a microtome for analysis.

10. The device of claim 1, wherein the reservoir is adapted to hold multiple articles.

11. The device of claim 1, wherein a computer readable label is affixed thereto.

12. The device of claim 1, wherein the specimen is analyzed by transmission electron microscopy, scanning electron microscopy, light microscopy, confocal microscopy, secondary ion mass spectroscopy, electron spectroscopy for chemical analysis, atom probe tomography or matrix-assisted laser desorption ionization.

13. The device of claim 1, further comprising a removable screen suitable for use as a microscope grid.

14. The device of claim 1, wherein the unitary reservoir is fabricated from a plastic selected from the group consisting of: polypropylene, polyethylene, polyvinyl chloride, polycarbonate, polyethylene terephthalate, polytetrafluoroethylene and combinations thereof.

15. A device for preparing specimens for microscopic analysis comprising a reservoir is adapted to fit inside a pipette tip and wherein filling the pipette tip with a fluid allows the fluid to enter the reservoir.

16. A device for preparing specimens for microscopic analysis comprising:
   a unitary reservoir the reservoir comprising;
   a) a first end adapted and configured to accept a pipette and a second end having an inlet/outlet therein;
   b) a screen provided in the second end;
   the reservoir being dimensioned and configured to mate with a second reservoir such that the first end of the first reservoir forms a liquid tight seal with the second end of a second reservoir; and
   the second end of the reservoir being dimensioned and configured to mate with a pipette tip; and
   the reservoir being configured to contain a specimen for microscopic evaluation and displacement of the pipette results in filling or emptying of the reservoir with one or more reagents; and
   the reservoir including a protrusion on the inner surface configured to break the surface tension of a liquid held in the reservoir;
   whereby filling the reservoir with the one or more reagents prepares the sample for microscopy.

17. The device of claim 16, wherein the reservoir is adapted to accept one or more grids.

18. The device of claim 17, wherein the one or more grids have a specimen attached thereto.

19. The device of claim 16, wherein, after fixation, the reservoir and specimen contained therein can be sectioned by a microtome for analysis.

20. The device of claim 16, wherein the microscopic analysis is performed with a light microscope, a scanning electron microscope, a transmission electron microscope, a confocal microscope, secondary ion mass spectroscopy, electron spectroscopy for chemical analysis, atom probe tomography or matrix-assisted laser desorption ionization.

21. The device of claim 16, wherein the first end is compatible with an adapter including an adapter usable to connect more than one fluid inlet to the reservoir.

22. The device of claim 16, wherein the reservoir is fabricated from a plastic selected from the group consisting of: polypropylene, polyethylene, polyvinyl chloride, polycarbonate, polyethylene terephthalate, polytetrafluoroethylene and combinations thereof.

* * * * *